United States Patent
Barnhorst et al.

(10) Patent No.: US 11,938,009 B2
(45) Date of Patent: Mar. 26, 2024

(54) DIAPER PRODUCT ADAPTED FOR COLLECTION OF EXUDATE SAMPLE FROM AN INFANT

(71) Applicant: The Procter & Gamble Company, Cincinnati, OH (US)

(72) Inventors: Jacob Alan Barnhorst, Cincinnati, OH (US); Jennifer Joan Gustin, Cincinnati, OH (US); Donald Carroll Roe, West Chester, OH (US); Kristian R. Santa Hornedo, Cincinnati, OH (US); Amy Lynn Tally, Cold Spring, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 266 days.

(21) Appl. No.: 17/458,638

(22) Filed: Aug. 27, 2021

(65) Prior Publication Data
US 2021/0386599 A1    Dec. 16, 2021

Related U.S. Application Data

(63) Continuation of application No. 16/016,973, filed on Jun. 25, 2018, now Pat. No. 11,135,104.
(Continued)

(51) Int. Cl.
*A61F 13/15* (2006.01)
*A61F 13/49* (2006.01)
(Continued)

(52) U.S. Cl.
CPC .. *A61F 13/51456* (2013.01); *A61F 13/49011* (2013.01); *A61F 13/495* (2013.01);
(Continued)

(58) Field of Classification Search
CPC .......... A61F 13/51456; A61F 13/49011; A61F 13/495; A61F 13/535; A61F 2013/4951; A61F 2013/4953; A61F 2013/51415
See application file for complete search history.

(56) References Cited

U.S. PATENT DOCUMENTS 2,610,629 A    9/1952  Hawkins
3,776,233 A    12/1973 Schaar
(Continued)

FOREIGN PATENT DOCUMENTS

CN    204274811 U    4/2015
EP    3072487 A1     9/2016
(Continued)

OTHER PUBLICATIONS

All Office Actions for U.S. Appl. No. 15/446,077.
(Continued)

*Primary Examiner* — Jacqueline F Stephens
(74) *Attorney, Agent, or Firm* — Daniel S. Albrecht

(57) ABSTRACT

Diapers adapted for use in the collection of stool samples from infants are disclosed. Such diapers may include a backsheet comprising an effectively liquid impermeable material, a liquid control structure disposed over the backsheet, and a pass-through port disposed at least partially in the rear portion of the diaper. The diaper may include other features adapted to contain exudates, isolate urine from fecal material following discharge, avoid absorption of liquid components of fecal material and enhance likelihood of collecting a fecal sample that is sufficiently representative of its composition immediately following discharge.

18 Claims, 24 Drawing Sheets

Related U.S. Application Data

(60) Provisional application No. 62/525,246, filed on Jun. 27, 2017.

(51) Int. Cl.
*A61F 13/495* (2006.01)
*A61F 13/514* (2006.01)
*A61F 13/535* (2006.01)

(52) U.S. Cl.
CPC .... *A61F 13/535* (2013.01); *A61F 2013/4951* (2013.01); *A61F 2013/4953* (2013.01); *A61F 2013/51415* (2013.01)

(56) References Cited

U.S. PATENT DOCUMENTS

| | | | |
|---|---|---|---|
| 4,231,370 A | 11/1980 | Mroz | |
| 4,257,418 A | 3/1981 | Hessner | |
| 4,629,643 A | 12/1986 | Curro | |
| 4,661,102 A | 4/1987 | Shikata et al. | |
| 5,026,364 A | 6/1991 | Robertson | |
| 5,226,992 A | 7/1993 | Morman | |
| 5,342,338 A | 8/1994 | Roe | |
| 5,516,572 A | 5/1996 | Roe | |
| 5,714,156 A | 2/1998 | Schmidt et al. | |
| 5,827,259 A | 10/1998 | Laux | |
| 5,906,604 A | 5/1999 | Roennberg et al. | |
| 5,931,827 A | 8/1999 | Buell et al. | |
| 5,934,470 A | 8/1999 | Bauer et al. | |
| 5,938,652 A | 8/1999 | Sauer | |
| 5,971,970 A | 10/1999 | Carlbark et al. | |
| 5,993,433 A | 11/1999 | St. Louis | |
| 5,998,695 A | 12/1999 | Roe et al. | |
| 6,010,490 A | 1/2000 | Freeland et al. | |
| 6,010,491 A | 1/2000 | Roe et al. | |
| 6,018,093 A | 1/2000 | Roe et al. | |
| 6,075,178 A | 6/2000 | La Wilhelm | |
| 6,120,486 A | 9/2000 | Toyoda et al. | |
| 6,132,410 A | 10/2000 | Gompel et al. | |
| 6,135,988 A | 10/2000 | Turner et al. | |
| 6,217,563 B1 | 4/2001 | Gompel et al. | |
| 6,296,862 B1 | 10/2001 | Paul et al. | |
| 6,315,764 B1 | 11/2001 | Faulks et al. | |
| 6,336,922 B1 | 1/2002 | Vangompel et al. | |
| 6,372,952 B1 | 4/2002 | Lash et al. | |
| 6,395,955 B1 | 5/2002 | Roe et al. | |
| 6,414,215 B1 | 7/2002 | Roe | |
| 6,471,716 B1 | 10/2002 | Pecukonis | |
| 6,491,677 B1 | 12/2002 | Glaug et al. | |
| 6,498,284 B1 | 12/2002 | Roe | |
| 6,551,295 B1 | 4/2003 | Schmidt et al. | |
| 6,570,057 B1 | 5/2003 | Schmidt et al. | |
| 6,603,403 B2 | 8/2003 | Jeutter et al. | |
| 6,627,786 B2 | 9/2003 | Roe et al. | |
| 6,638,262 B2 | 10/2003 | Suzuki et al. | |
| 6,659,993 B2 | 12/2003 | Minato | |
| 6,664,439 B1 | 12/2003 | Arndt et al. | |
| 6,680,422 B2 | 1/2004 | Roe | |
| 6,716,205 B2 | 4/2004 | Coenen et al. | |
| 6,720,471 B1 | 4/2004 | Arndt et al. | |
| 6,767,344 B2 | 7/2004 | Suzuki | |
| 6,786,895 B1 | 9/2004 | Schmitz | |
| 6,790,203 B2 | 9/2004 | Een | |
| 6,817,993 B1 | 11/2004 | Simmons et al. | |
| 6,921,394 B2 | 7/2005 | Sayama et al. | |
| 6,989,187 B2 | 1/2006 | Thomas | |
| 7,033,340 B1 | 4/2006 | Muscat et al. | |
| 7,118,557 B2 | 10/2006 | Minato et al. | |
| 7,159,532 B2 | 1/2007 | Klofta et al. | |
| 7,163,530 B1 | 1/2007 | Toyoshima et al. | |
| 7,332,642 B2 | 2/2008 | Liu | |
| 7,419,562 B2 | 9/2008 | Van Gompel | |
| 7,566,330 B2 | 7/2009 | Sugiyama et al. | |
| 7,666,173 B2 | 2/2010 | Mishima et al. | |
| 7,695,463 B2 | 4/2010 | Lavon et al. | |
| 7,744,576 B2 | 6/2010 | Busam | |
| 7,753,899 B2 | 7/2010 | Mori et al. | |
| 7,772,455 B1 | 8/2010 | Roe et al. | |
| 7,785,309 B2 | 8/2010 | Van Gompel et al. | |
| 7,794,441 B2 | 9/2010 | Ashton et al. | |
| 7,838,722 B2 | 11/2010 | Blessing et al. | |
| 7,838,723 B1 | 11/2010 | Schmidt et al. | |
| 7,879,017 B1 | 2/2011 | Tabata | |
| 8,017,827 B2 | 9/2011 | Hundorf et al. | |
| 8,043,272 B2 | 10/2011 | Long et al. | |
| 8,178,748 B2 | 5/2012 | Hammons et al. | |
| 8,180,603 B2 | 5/2012 | Blessing et al. | |
| 8,181,278 B2 | 5/2012 | Odorzynski et al. | |
| 8,216,201 B2 | 7/2012 | Beck | |
| 8,231,592 B2 | 7/2012 | Suzuki et al. | |
| 8,274,393 B2 | 9/2012 | Ales et al. | |
| 8,430,858 B2 | 4/2013 | Baeck | |
| 8,449,518 B2 | 5/2013 | Allison-rogers | |
| 8,496,637 B2 | 7/2013 | Hundorf et al. | |
| 8,502,012 B2 | 8/2013 | Meyer et al. | |
| 8,581,019 B2 | 11/2013 | Carlucci et al. | |
| 8,598,406 B2 | 12/2013 | Ponomarenko et al. | |
| 8,618,349 B2 | 12/2013 | Klofta | |
| 8,668,680 B2 | 3/2014 | Ichikawa et al. | |
| 8,679,391 B2 | 3/2014 | O'donnell et al. | |
| 8,747,380 B2 | 6/2014 | Coates | |
| 8,764,721 B2 | 7/2014 | Van Gompel | |
| 8,764,722 B2 | 7/2014 | Rhein et al. | |
| 8,894,626 B2 | 11/2014 | Beck | |
| 8,926,580 B2 | 1/2015 | Carney et al. | |
| 8,927,801 B2 | 1/2015 | Klofta | |
| 8,929,944 B2 | 1/2015 | Yam | |
| 8,933,292 B2 | 1/2015 | Abraham et al. | |
| 8,939,562 B2 | 1/2015 | Koike et al. | |
| 8,968,614 B2 | 3/2015 | Desai et al. | |
| 8,968,814 B2 | 3/2015 | Heino et al. | |
| 8,979,815 B2 | 3/2015 | Roe et al. | |
| 8,992,496 B2 | 3/2015 | Bäck | |
| 9,044,358 B2 | 6/2015 | Nakajima et al. | |
| 9,050,218 B2 | 6/2015 | Martynus et al. | |
| 9,050,219 B2 | 6/2015 | Martynus et al. | |
| 9,060,904 B2 | 6/2015 | Hundorf et al. | |
| 9,072,634 B2 | 7/2015 | Hundorf et al. | |
| 9,125,758 B2 | 9/2015 | Skreosen | |
| 9,168,181 B2 | 10/2015 | Popp et al. | |
| 9,216,116 B2 | 12/2015 | Roe et al. | |
| 9,241,839 B2 | 1/2016 | Abraham et al. | |
| 9,259,362 B2 | 2/2016 | Popp et al. | |
| 9,333,120 B2 | 5/2016 | Lavon et al. | |
| 9,445,951 B2 | 9/2016 | Moberg-alehammar et al. | |
| 9,464,369 B2 | 10/2016 | Isele et al. | |
| 9,486,368 B2 | 11/2016 | Nelson | |
| 9,554,948 B2 | 1/2017 | Song et al. | |
| 9,675,503 B2 | 6/2017 | Carney | |
| 9,713,557 B2 | 7/2017 | Arizti et al. | |
| 9,789,009 B2 | 10/2017 | Joseph | |
| 2001/0053902 A1 | 12/2001 | Roe et al. | |
| 2002/0013568 A1* | 1/2002 | Cinelli | A61L 15/58 604/387 |
| 2002/0035354 A1 | 3/2002 | Mirle et al. | |
| 2002/0091368 A1 | 7/2002 | Beck et al. | |
| 2002/0111596 A1 | 8/2002 | Fletcher | |
| 2003/0050616 A1 | 3/2003 | Reynolds et al. | |
| 2003/0135176 A1 | 7/2003 | Delzer et al. | |
| 2003/0212376 A1 | 11/2003 | Walter | |
| 2004/0102757 A1 | 5/2004 | Olson | |
| 2004/0158213 A1 | 8/2004 | Ponomarenko et al. | |
| 2004/0230171 A1 | 11/2004 | Ando | |
| 2004/0254549 A1 | 12/2004 | Olson et al. | |
| 2005/0215962 A1 | 9/2005 | Litvay et al. | |
| 2006/0004340 A1 | 1/2006 | Ben-natan | |
| 2006/0048880 A1 | 3/2006 | Blessing | |
| 2006/0247597 A1 | 11/2006 | Hogan et al. | |
| 2006/0264858 A1 | 11/2006 | Roe | |
| 2007/0049895 A1 | 3/2007 | Van Gompel et al. | |
| 2007/0088310 A1 | 4/2007 | Sugiyama et al. | |
| 2007/0093767 A1 | 4/2007 | Carlucci et al. | |
| 2007/0232180 A1 | 10/2007 | Polat et al. | |
| 2007/0233027 A1 | 10/2007 | Roe et al. | |

(56) References Cited

U.S. PATENT DOCUMENTS

| | | |
|---|---|---|
| 2008/0091159 A1 | 4/2008 | Carlucci et al. |
| 2008/0269706 A1 | 10/2008 | Long et al. |
| 2008/0269707 A1 | 10/2008 | Song |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf |
| 2008/0312623 A1 | 12/2008 | Hundorf et al. |
| 2008/0312625 A1 | 12/2008 | Hundorf et al. |
| 2008/0312628 A1 | 12/2008 | Hundorf et al. |
| 2009/0138884 A1 | 5/2009 | Kakeda et al. |
| 2009/0318884 A1 | 12/2009 | Meyer et al. |
| 2010/0030173 A1 | 2/2010 | Song et al. |
| 2011/0015602 A1 | 1/2011 | Schmidt et al. |
| 2011/0137274 A1 | 6/2011 | Klofta |
| 2011/0184372 A1 | 7/2011 | Esping |
| 2012/0032319 A1 | 2/2012 | Dunipace |
| 2012/0035578 A1 | 2/2012 | Yamanaka et al. |
| 2012/0141128 A1 | 6/2012 | Bai et al. |
| 2012/0277713 A1 | 11/2012 | Raycheck |
| 2012/0316526 A1 | 12/2012 | Rosati et al. |
| 2012/0316528 A1 | 12/2012 | Kreuzer et al. |
| 2012/0323195 A1 | 12/2012 | Ehrnsperger et al. |
| 2013/0006206 A1* | 1/2013 | Wada ............... A61F 13/535 604/385.01 |
| 2013/0079740 A1 | 3/2013 | Ehrnsperger et al. |
| 2013/0110065 A1 | 5/2013 | Takahashi et al. |
| 2013/0116644 A1 | 5/2013 | Wei et al. |
| 2013/0137274 A1 | 5/2013 | Takahashi |
| 2013/0331806 A1 | 12/2013 | Rosati et al. |
| 2014/0005622 A1 | 1/2014 | Wirtz |
| 2014/0005623 A1 | 1/2014 | Wirtz et al. |
| 2014/0068839 A1 | 3/2014 | Steele et al. |
| 2014/0107605 A1 | 4/2014 | Schroer, Jr. |
| 2014/0121487 A1 | 5/2014 | Faybishenko et al. |
| 2014/0142528 A1 | 5/2014 | Wang et al. |
| 2014/0142529 A1 | 5/2014 | Cheng |
| 2014/0155856 A1 | 6/2014 | Ronnberg et al. |
| 2014/0163501 A1 | 6/2014 | Ehrnsperger et al. |
| 2014/0163503 A1 | 6/2014 | Arizti |
| 2014/0221956 A1 | 8/2014 | Martynus et al. |
| 2014/0303589 A1 | 10/2014 | Paz et al. |
| 2014/0336605 A1 | 11/2014 | Hardie et al. |
| 2014/0345034 A1 | 11/2014 | Hansson et al. |
| 2014/0350508 A1 | 11/2014 | Popp |
| 2014/0371701 A1 | 12/2014 | Bianchi |
| 2015/0045759 A1 | 2/2015 | Martynus et al. |
| 2015/0045760 A1 | 2/2015 | Martynus et al. |
| 2015/0045761 A1 | 2/2015 | Martynus et al. |
| 2015/0051510 A1 | 2/2015 | Husmark et al. |
| 2015/0065973 A1 | 3/2015 | Roe et al. |
| 2015/0088086 A1 | 3/2015 | Beck |
| 2015/0157251 A1 | 6/2015 | Nelson |
| 2015/0173968 A1 | 6/2015 | Joseph |
| 2015/0209195 A1 | 7/2015 | Martynus et al. |
| 2015/0223996 A1 | 8/2015 | Martynus et al. |
| 2015/0257946 A1 | 9/2015 | Martynus et al. |
| 2015/0273793 A1 | 10/2015 | Thomas |
| 2015/0282997 A1 | 10/2015 | Arizti |
| 2015/0282998 A1 | 10/2015 | Arizti et al. |
| 2015/0282999 A1 | 10/2015 | Arizti |
| 2015/0313770 A1 | 11/2015 | Hubbard, Jr. et al. |
| 2016/0038350 A1 | 2/2016 | Martynus |
| 2016/0278992 A1 | 9/2016 | Martynus et al. |
| 2016/0278993 A1 | 9/2016 | Martynus et al. |
| 2016/0278994 A1 | 9/2016 | Martynus et al. |
| 2016/0303275 A1 | 10/2016 | Joseph et al. |
| 2017/0003257 A1 | 1/2017 | Klofta et al. |
| 2017/0246052 A1 | 8/2017 | Ludwig |
| 2017/0252015 A1 | 9/2017 | Barnhorst |
| 2017/0252233 A1 | 9/2017 | Barnhorst |
| 2018/0368817 A1 | 12/2018 | Tally et al. |
| 2018/0369029 A1 | 12/2018 | Barnhorst et al. |

FOREIGN PATENT DOCUMENTS

| | | |
|---|---|---|
| ES | 1170784 Y | 2/2017 |
| FR | 122985 | 9/1960 |
| FR | 1229858 A | 9/1960 |
| FR | 77546 E | 3/1962 |
| JP | H10295723 A | 11/1998 |
| KR | 20100086255 A | 1/2009 |
| WO | 199856327 A1 | 12/1998 |
| WO | 09155265 A2 | 12/2009 |
| WO | 2016122152 A1 | 8/2016 |

OTHER PUBLICATIONS

All Office Actions for U.S. Appl. No. 16/002,244.
All Office Actions for U.S. Appl. No. 16/016,973.
Search Report and Written Opinion for PCT/US2018/039241 dated Oct. 8, 2018.
All Office Actions for U.S. Appl. No. 15/234,540 filed Aug. 11, 2016.
All Office Actions for U.S. Appl. No. 15/440,012, filed Feb. 23, 2017.
All Office Actions, U.S. Appl. No. 15/234,235.
All Office Actions, U.S. Appl. No. 15/446,450.
Print of page bearing heading "Marian Medical, Inc.," and bearing date Aug. 11, 2013 (2 pages).
Print of page bearing heading "Marian Medical, Inc.," and bearing date Feb. 13, 2017 (2 pages).
Website: htt.n:/ /l,v1.vw .small-beginnings.corn/#! bJ ank!co.nk, Phototherapy Diapers'Beary Small' Bili-Buns, 2015.
All Office Actions; U.S. Appl. No. 17/463,580, filed Sep. 1, 2021.
Unpublished U.S. Appl. No. 17/463,580, filed Sep. 1, 2021, to Jacob Alan Barnhorst et al.
All Office Actions; U.S. Appl. No. 17/555,993, filed Dec. 20, 2021.
Unpublished U.S. Appl. No. 17/555,993, filed Dec. 20, 2021, to Jacob Alan Barnhorst et al.

* cited by examiner

DIAPER PRODUCT ADAPTED FOR COLLECTION OF EXUDATE SAMPLE FROM AN INFANT

CROSS REFERENCE TO RELATED APPLICATION

This application is a continuation of U.S. application Ser. No. 16/016,973, filed on Jun. 25, 2018, which claims the benefit of U.S. Provisional Patent Application No. 62/525,246, filed on Jun. 27, 2017, the entire disclosure of which is fully incorporated herein by reference.

BACKGROUND

Collection of urine samples from infants is sometimes desired for medical diagnostic or research purposes, for example, to identify or study characteristics or effects of medical conditions such as infections, allergies, presence of drugs in the infants' systems, or other conditions. Urine can be tested to yield information relating to kidney function, electrolyte balance and some illnesses and infections. Testing for the presence of drugs in newborn babies is increasingly desired, as problems associated with maternal drug abuse are coming under greater scrutiny; analysis of urine samples is a commonly used testing method. Typically in such circumstances it is desired to obtain a sample that is free of contamination by fecal matter or other substances that may contact the urine after urination. It is also typically desired that the urine sample is intact, in that quantities or water or other constituents have not been removed by, e.g., evaporation or absorption into, e.g., absorbent components of a diaper.

Similarly, collection of stool samples from infants is sometimes desired for medical diagnostic or research purposes, for example, to identify or study characteristics or effects of medical conditions such as infections, allergies or other conditions. Typically in such circumstances it is desired to obtain a stool sample that is uncontaminated and intact, i.e., has not been contaminated by urine or any other substance, and has not had any of its constituents removed by, e.g., absorption into a diaper.

Particularly in young infants, urination is usually not sufficiently predictable to provide warning or time for a caregiver to prepare to collect an uncontaminated and intact sample at the time urination occurs. Similarly, a bowel movement is usually not sufficiently predictable to provide warning or time for a caregiver to prepare to collect an uncontaminated and intact stool sample immediately after elimination occurs. An attempt at collection some period of time after elimination substantially increases the risk that the sample will be non-representative. Additionally, it may be undesirable to allow fecal material to be in contact with relatively sensitive and/or delicate skin of very young infants, to any substantial extent or for any substantial period of time.

There are currently various devices and methods that that have been adopted by health care professionals to collect urine samples. These have included inserting extra absorbent material (such as cotton wadding) into a diaper proximate the discharge location; following a urine discharge, the material may be removed from the diaper and compressed to expel the absorbed urine into a sample container. Other methods have involved use of catheters (internal and external). These methods have not been entirely satisfactory; they have been deemed overly cumbersome, messy, or undesirably uncomfortable and/or invasive for the infant patient.

Anticipatory methods and devices for stool sample collection used to date, also, have included undesirably invasive devices and steps, e.g., use of catheters or bag devices, or have been deemed difficult, messy, hazardous and/or unreliable. Additionally, devices such as bag devices have often involved use of adhesive to affix them to the patient's skin. Particularly for premature and very young infants this may be unsatisfactory because these patients typically have very sensitive and delicate skin, which can be painfully irritated and even damaged by use of adhesives.

Currently available disposable absorbent diapers are not satisfactory for collecting uncontaminated and intact urine samples, because they do not isolate urine from fecal matter; they absorb aqueous liquid relatively quickly and do not readily release it; and they often include materials that can contaminate a urine sample and/or otherwise render it non-representative of its composition immediately following urination.

Similarly, disposable diapers of conventional design are unsuitable as stool sample collection devices because they are designed to rapidly absorb and retain liquid exudates in an absorbent structure. Any stool in a conventional diaper that remains unabsorbed upon removal of the diaper from the infant will have had much of its liquid content removed by absorption into the absorbent structure, rendering it non-representative of its original composition.

Therefore, there is room for improvement to methods and/or devices by which uncontaminated and intact urine and/or stool samples may be collected from infants for purposes of medical diagnosis, research, etc.

DESCRIPTION OF EXAMPLES

Definitions

Figure 1:
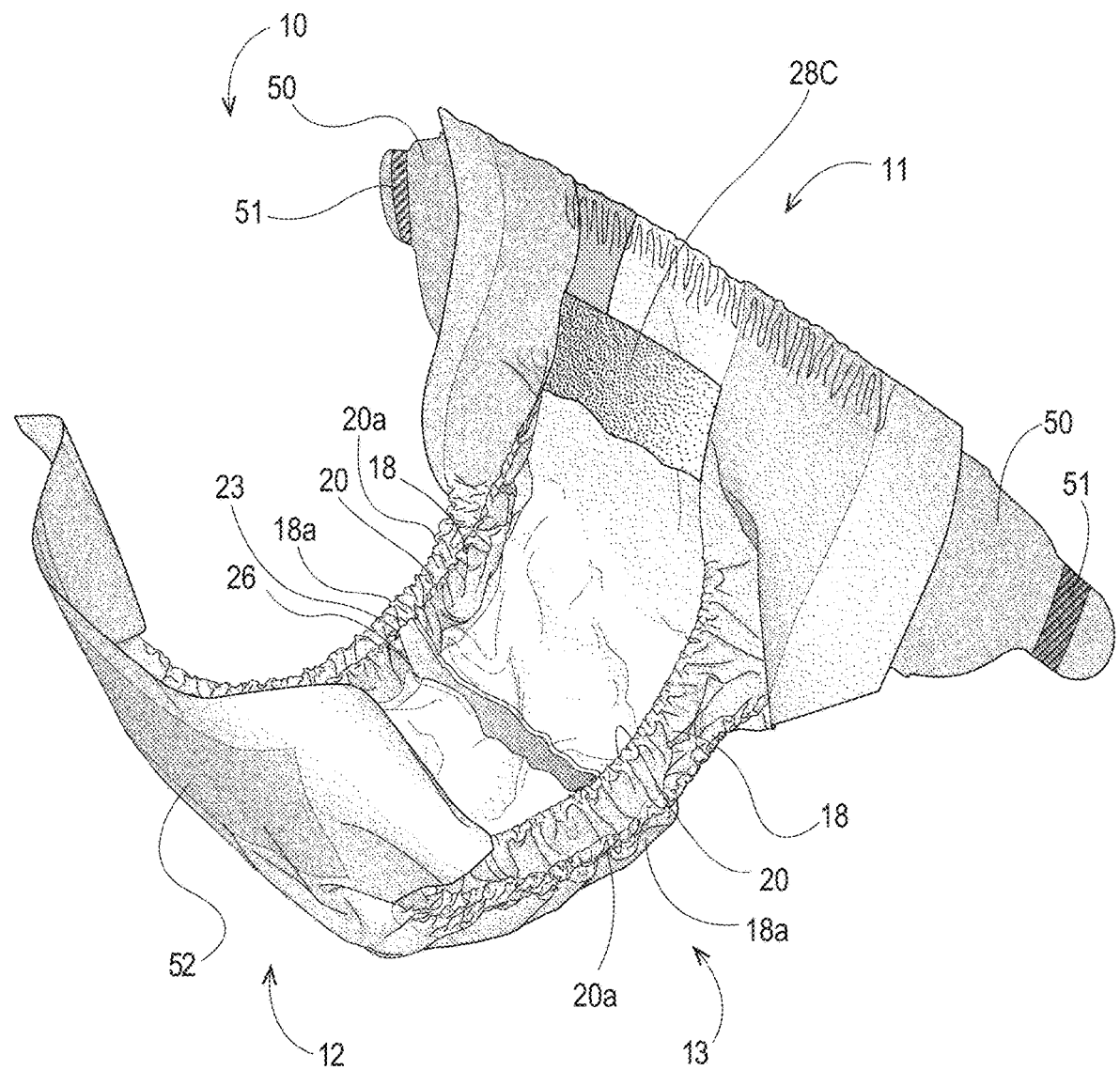
FIG. 1 is a perspective view of a diaper in a relaxed, opened position as it might appear resting on a table, wearing-facing side up.

The term "hydrophilic" describes surfaces such as film or fiber surfaces, which are wettable by aqueous fluids (e.g., aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e., hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic/non-wettable if the contact angle is greater than 90° and the fluid does not spread spontaneously across the surface of the fiber.

The "liquid control structure" of a diaper includes all components and structure overlying a liquid impermeable backsheet, and disposed along and straddling the longitudinal axis of the diaper, except for a liquid permeable topsheet. If the diaper includes a topsheet, the liquid control structure includes all components and structure disposed between the backsheet and the topsheet, and disposed along and straddling the longitudinal axis of the diaper. An absorbent core structure as typically appears in currently marketed disposable diapers is one type of "liquid control structure" as the latter term is used herein; however, a "liquid control structure" as the term is more broadly used herein may retainably absorb aqueous liquid, as will an absorbent core structure of a typical diaper, or may, alternatively, be adapted not to, or have a portion adapted not to, retainably absorb aqueous liquid in portions or in the entirety thereof. The liquid control structure of a diaper has a plan surface area when the diaper is laid out in extended and flat configuration on a horizontal surface, viewed from above along a direction orthogonal to the surface. The plan surface area also defines a volume of space, coextensive with the plan surface area in the x-y plane and quantified by the plan surface area and the average z-direction caliper or thickness of the liquid control structure.

Lateral," "transverse," and forms thereof, with respect to a diaper or a component thereof, refers to a direction generally parallel to the waist edges of the diaper.

"Length," with respect to a diaper or a component thereof, refers to a dimension measured along a direction generally perpendicular to the waist edges of the diaper.

"Longitudinal," and forms thereof, with respect to a diaper or a component thereof, refers to a direction generally perpendicular to the waist edges of the diaper.

"Width," with respect to a diaper or a component thereof, refers to a dimension measured along a direction generally parallel to the waist edges of the diaper.

"Liquid impermeable," with respect to a sheet or layer component of a diaper positioned to receive urine or fecal exudate, means that liquid components of the exudate will not pass through the sheet or layer from one side to the other, without application of an amount of pressure, exceeding atmospheric level, to the liquid as it contacts the sheet or layer. A liquid impermeable sheet or layer of material may be formed of a continuous, unapertured and non-porous polymer film; or a polymer film with apertures or pores that are sufficiently small in combination with sufficient hydrophobic surface properties of the polymer such that the liquid will not pass through the apertures or pores without application of pressure; or a fibrous nonwoven web material having a combination of sufficiently small interstitial/inter-fiber spaces or pores and sufficient hydrophobic surface properties of the fibers such that the liquid will not pass through the apertures or pores without application of pressure. An apertured or porous sheet or layer of material may be liquid impermeable as defined above, but may be permeable to water vapor.

"Liquid permeable," with respect to a sheet or layer component of a diaper positioned to receive urine or fecal exudate, means that liquid components of the exudate will pass through the sheet or layer from one side to the other, without application of an amount of pressure, exceeding atmospheric level, to the liquid as it contacts the sheet or layer. A liquid permeable sheet or layer of material may be formed of a polymer film, having apertures or pores that are sufficiently large, and/or having sufficiently hydrophilic surface properties, such that the liquid will pass through the apertures or pores without application of pressure. A liquid permeable sheet or layer of material may be formed of a fibrous nonwoven web material, having sufficiently large apertures, interstitial/interfiber spaces or pores, and/or having sufficiently hydrophilic surface properties of the fibers, such that the liquid will pass through the apertures or interstitial/interfiber spaces or pores without application of pressure.

A "nonwoven" web material is a manufactured web of directionally or randomly oriented fibers consolidated into a web and bonded by friction, entanglement, thermal bonding, mechanical bonding, cohesion and/or adhesion, or any combination thereof. The term excludes film, paper and products which are woven, knitted or stitch-bonded. The fibers may be of natural or man-made (synthetic) origin. They may be staple fibers or continuous fibers. Nonwoven fabrics can be formed by processes such as but not limited to meltblowing, spunbonding, dry-laying, wet-laying and carding, and combinations thereof. The basis weight of nonwoven web materials is usually expressed in grams per square meter (gsm).

"Inboard" and "outboard" are relative terms relating the locations of two features of a diaper with respect to a longitudinal axis of the diaper. A first feature of a diaper is inboard of a second feature of the diaper, and the second feature is outboard of the first feature, when the first feature lies closer to the longitudinal axis of the diaper than the second feature.

"Underlie" and "overlie" (and forms thereof) refer to a vertical positional relationship between two components of a diaper that is open, extended and laid out flat on a horizontal surface with the wearer-facing surfaces facing up. With the diaper in this position, a first component overlies a second component, and the second component underlies the first component, when the first component lies directly or indirectly over or on top of the second component, or the second component lies directly or indirectly beneath the first component.

The terms "upper" and "lower," and forms thereof, used with respect to components of a diaper, relate to the vertical direction and positioning of the components when the diaper is open, extended and laid out flat on a horizontal surface with the wearer-facing surfaces facing up. With respect to FIGS. 5, 6A, 6B, 8, 13A, 13B, 14A and 14B, the uppermost components are depicted nearest the top of the page and the lowermost components are nearest the bottom of the page.

Figure 12:
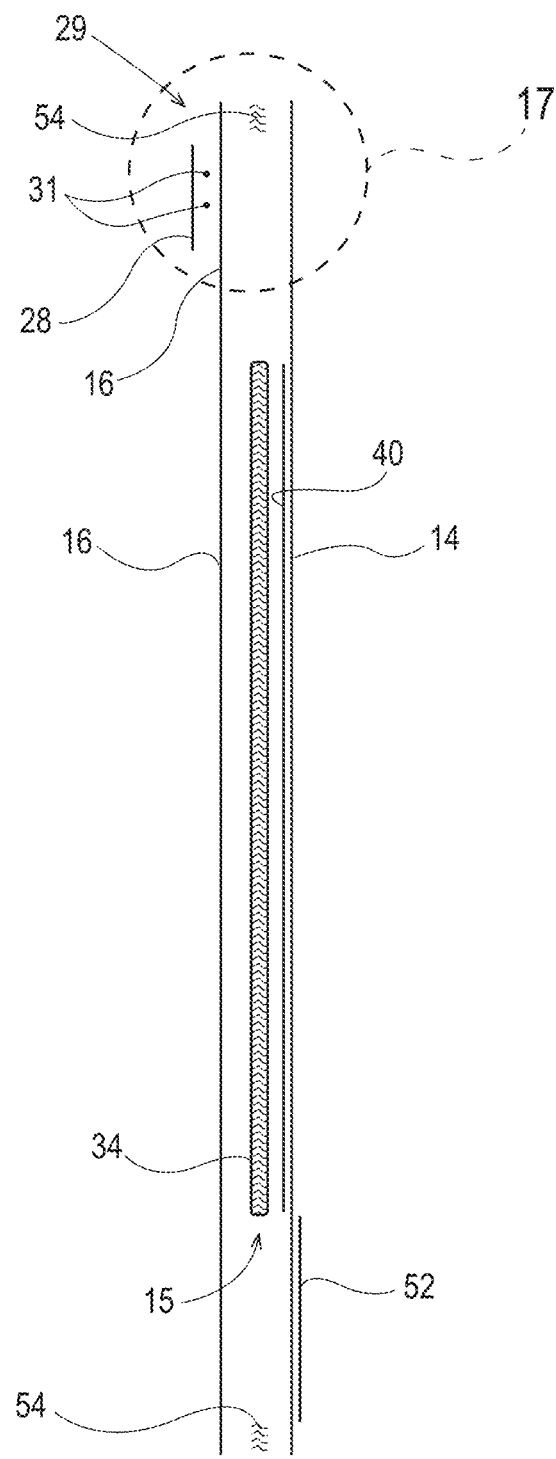
FIG. 12 is a schematic, exploded longitudinal cross-section of one example of an example of a diaper as shown in FIG. 10A, taken along line 12-12 shown in FIG. 10A.
Figure 13A:
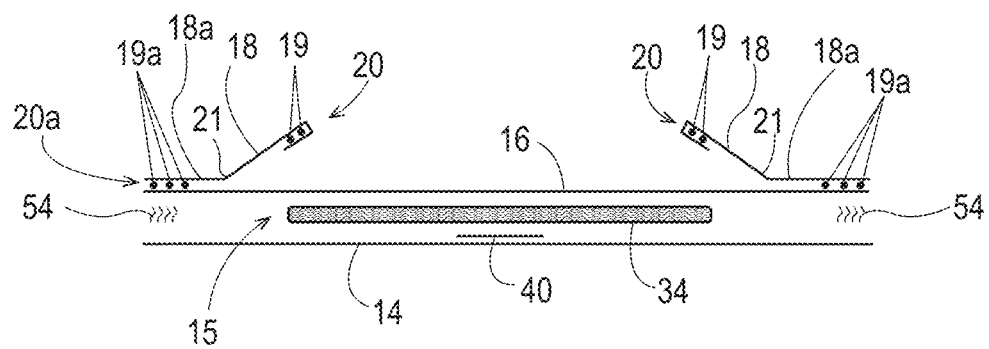
FIG. 13A is a schematic, exploded lateral cross-section of a diaper as shown in FIG. 10A, taken along line 13A-13A shown in FIG. 10A.
Figure 13B:
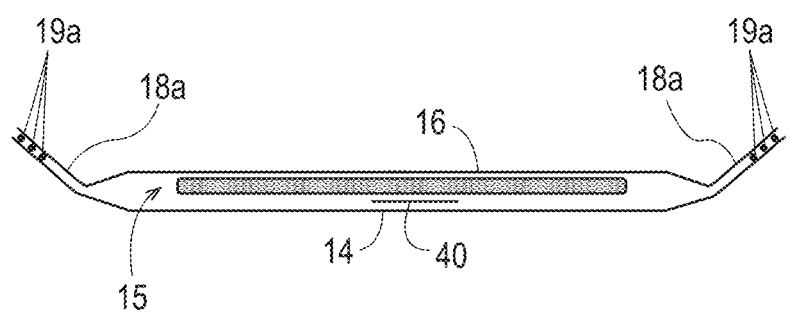
FIG. 13B is a schematic, exploded lateral cross-section of a diaper as shown in FIG. 10B, taken along line 13B-13B shown in FIG. 10B.

"Wearer-facing," with respect to a diaper or a component thereof, means the side of the diaper or component that faces the wearer's body when the diaper is worn in its normal configuration, with the backsheet to the outside. "Outward-facing" means the side of the diaper or component that faces away from the wearer when the diaper is worn in its normal configuration. In FIGS. 4A-4D, the wearer-facing side of each component is depicted to the left, and the outward-facing side of each component is depicted to the right. In FIGS. 5, 6A, 6B and 8, the wearer-facing side of each component is depicted toward the top of each figure, and the outward-facing side is toward the bottom. In FIG. 12, the wearer-facing side of each component depicted is to the left, and the outward-facing side of each component is to the right. In FIGS. 13A, 13B, 14A and 14B, the wearer-facing side of each component depicted is toward the top of each figure, and the outward-facing side is toward the bottom.

"x-y plane", used with respect to a diaper, relates to a plane parallel to a horizontal surface upon which the diaper may be opened, extended and laid out flat with the wearer-facing surfaces facing up. With respect to FIGS. 2A, 2B, 3A, 3B, 7, 10A, 10B and 11, the plane of the page is an x-y plane.

"z-direction," used with respect to a diaper, relates to the direction orthogonal to the x-y plane. With respect to FIGS. 2A, 2B, 3A, 3B, 7, 10A, 10B and 11, the z-direction is the direction orthogonal to the plane of the page.

Examples of Features That May be Useful for Diapers for Purposes Herein

Referring generally to FIGS. 1, 2A, 3A, 4A, 9, 10A and 12, a diaper 10 may have an outward-facing backsheet 14 and a wearer-facing topsheet 16. Backsheet 14 and topsheet 16 may be affixed together either directly, or with other layers interposed therebetween, to form an enveloped space therebetween. In one example, backsheet 14 and topsheet 16 may be affixed together partially or entirely about their peripheries by deposits of adhesive 54.

Fastening System

Diaper 10 may including a pair of fastening members 50 extending laterally outboard of the main structure in the rear portion 11. Fastening members 50 may be integral and/or contiguous with other components forming the diaper (such as the backsheet and/or topsheet), or may be separately formed and attached via bonds 53 as suggested in FIGS. 2A, 3A, 10A, 10B and 11. Fastening members 50 may be formed of a nonwoven web material, a polymer film material (which may be elastomeric), a laterally elastically stretchable stretch laminate material, or any other web/sheet material having lateral tensile strength suitable for sustaining lateral tensile forces present when the diaper is fastened about an intended wearer. Each fastening member may have affixed thereon a fastening component 51 such as a patch of hooks, forming a component of a hook-and loop fastening system; alternatively, fastening component 51 may be a patch of material bearing adhesive, or any other suitable fastening mechanism. A corresponding receiving material such as patch of loops material or adherent material that effectively contacts and fastenably attaches to the adhesive-bearing material may be included on the outer side of front portion 12 of the diaper at a landing zone 52. It will be appreciated that other types of fastening components and fastening systems are known and may be used as an alternative to a hook-and-loop or adhesive fastening system.

Backsheet

Diaper 10 may have an outer backsheet 14 that forms most of the outward-facing surfaces of the diaper when worn. Backsheet 14 may be liquid impermeable and may be formed of a single layer of material or may be formed of a laminate of two or more layers of material. In one example, backsheet 14 may be formed of an inner layer of an effectively liquid impermeable polymeric film, laminated with an outer layer of a nonwoven web material. An outer layer of nonwoven material may be included for purposes of enhancing tensile strength of the backsheet and/or for imparting a softer, more cloth-like feel and appearance to the backsheet. In another example, an effectively liquid impermeable backsheet may be formed of a nonwoven web material alone, having at least a layer of closely-spaced, fine fibers such as meltblown fibers that are hydrophilic, e.g., in a spunbond-meltblown-spunbond (SMS) layered configuration. In a simpler example, backsheet 14 may be formed of a layer of polymeric film alone.

In conventional disposable diapers, it is often desired that the backsheet have high opacity, for aesthetic purposes of concealment of the presence of exudates contained in the diaper during wear. However, for the special purposes contemplated herein, i.e., timely collection of exudates samples, it may be desired that the backsheet have sufficient translucency or even transparency, and in some examples color neutrality, to enable easy visual detection of the presence of stool and/or urine therein.

Manipulation of opacity (conversely, translucency) by selection of material components, opacifying additives, and manufacturing techniques is well known in the art. For purposes of decreasing opacity/increasing translucency, opacifying and/or whitening additives (such as, for example, TiO2), and/or coloring agents (i.e. dyes, pigments) may be minimized or even omitted entirely from the materials constituting the backsheet. Clarifying additives may be included in the resin formulations used to form the backsheet materials, e.g., backsheet film and/or nonwoven fibers. For purposes described above, it may be desired that the backsheet have an opacity no greater than 50 percent, more preferably no greater than 45 percent, even more preferably no greater than 40 percent, and still more preferably no greater than 35 percent, as measured by the opacity test method described below.

Longitudinal Cuffs

Diaper 10 may include a pair of standing longitudinal cuffs 18. Such cuffs are currently common in disposable diapers and are variously known as gasketing cuffs, standing cuffs, barrier cuffs, etc. Longitudinal cuffs 18 may be formed of a fibrous nonwoven material, a polymeric film material, or a laminate thereof. In one example, longitudinal cuffs 18 may be formed of an effectively liquid impermeable material, which will serve to prevent escape of liquid constituents of stool collected in the diaper. Non-limiting examples of suitable materials for forming longitudinal cuffs are described in U.S. Pat. No. 7,695,463.

As reflected in FIGS. 5, 6A, 6B, 13A and 13B, longitudinal cuffs 18 may each have a proximal portion 21 affixed to an underlying component of the diaper structure such as a topsheet and/or backsheet, and a free longitudinal distal edge 20. Each cuff 18 may be longitudinally affixed along the proximal portion 21 to the diaper structure by mechanical or thermal bonding, by adhesive or other means, or a combination thereof, however, use of adhesive to bond or supplementally bond proximal portions 21 to the structure may serve to provide a liquid seal at the junction between the cuff 18 and the underlying component. In one example, the proximal portion 21 of the cuff 18 is bonded to the topsheet 16, 16f and/or 16r with a continuous application of adhesive therebetween, to provide a liquid seal at the junction. The adhesive may be a hot-melt type adhesive conventionally used in the manufacture of disposable diapers.

Figure 2A:
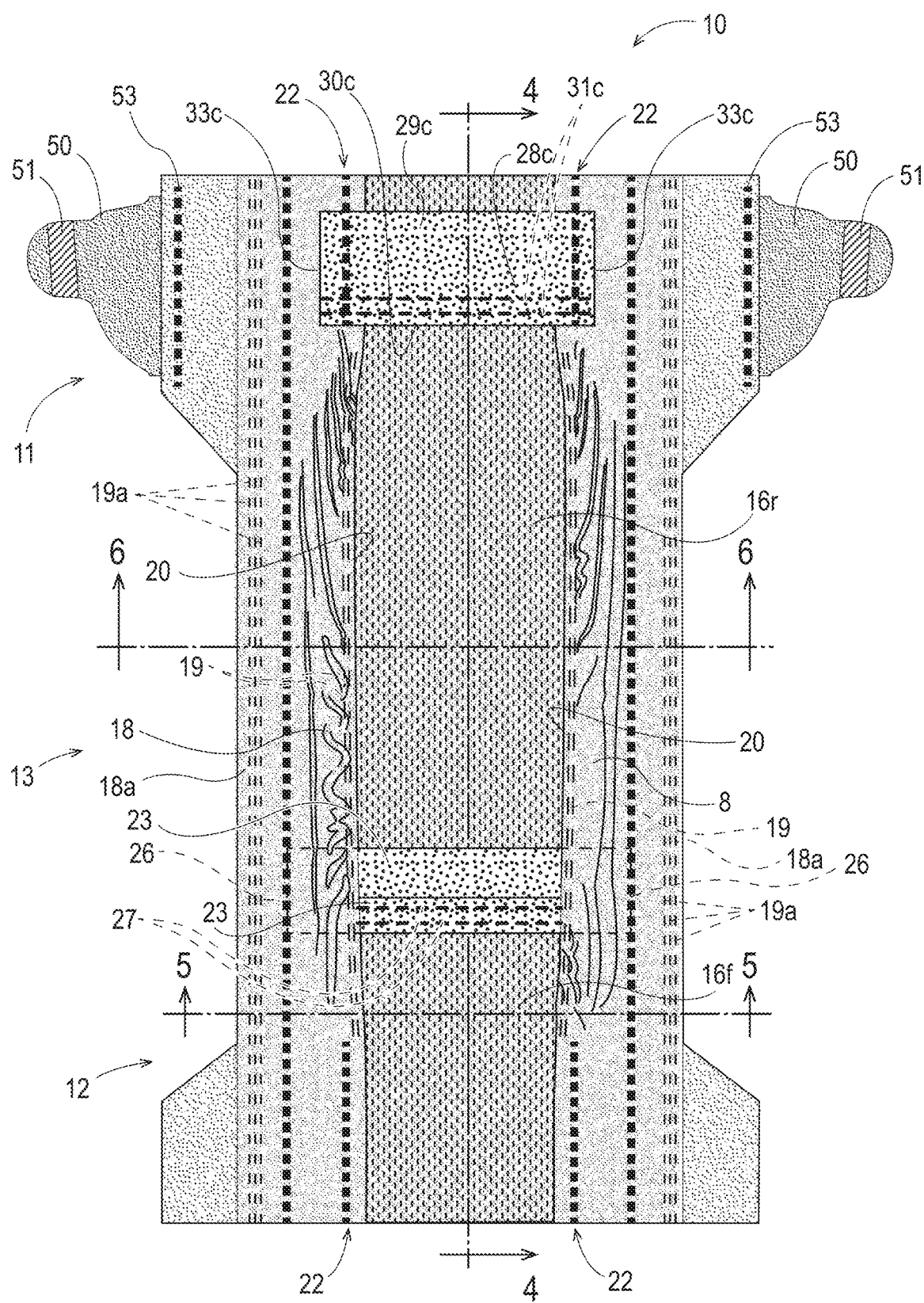
FIG. 2A is a plan view of a diaper in an extended and flat condition, with the wearer-facing surfaces facing the viewer.
Figure 2B:
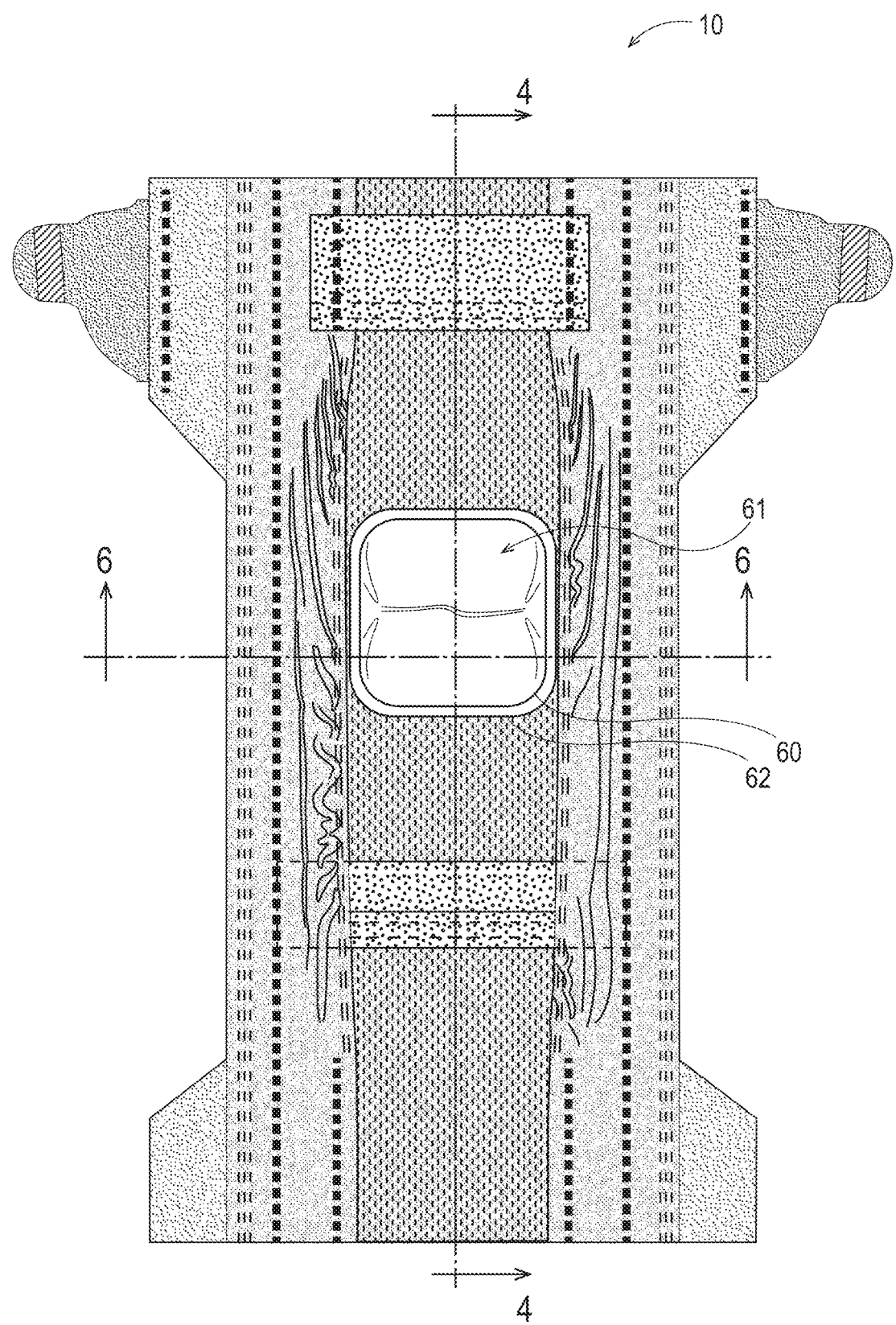
FIG. 2B is a plan view of another example of a diaper in an extended and flat condition, with the wearer-facing surfaces facing the viewer.
Figure 9:
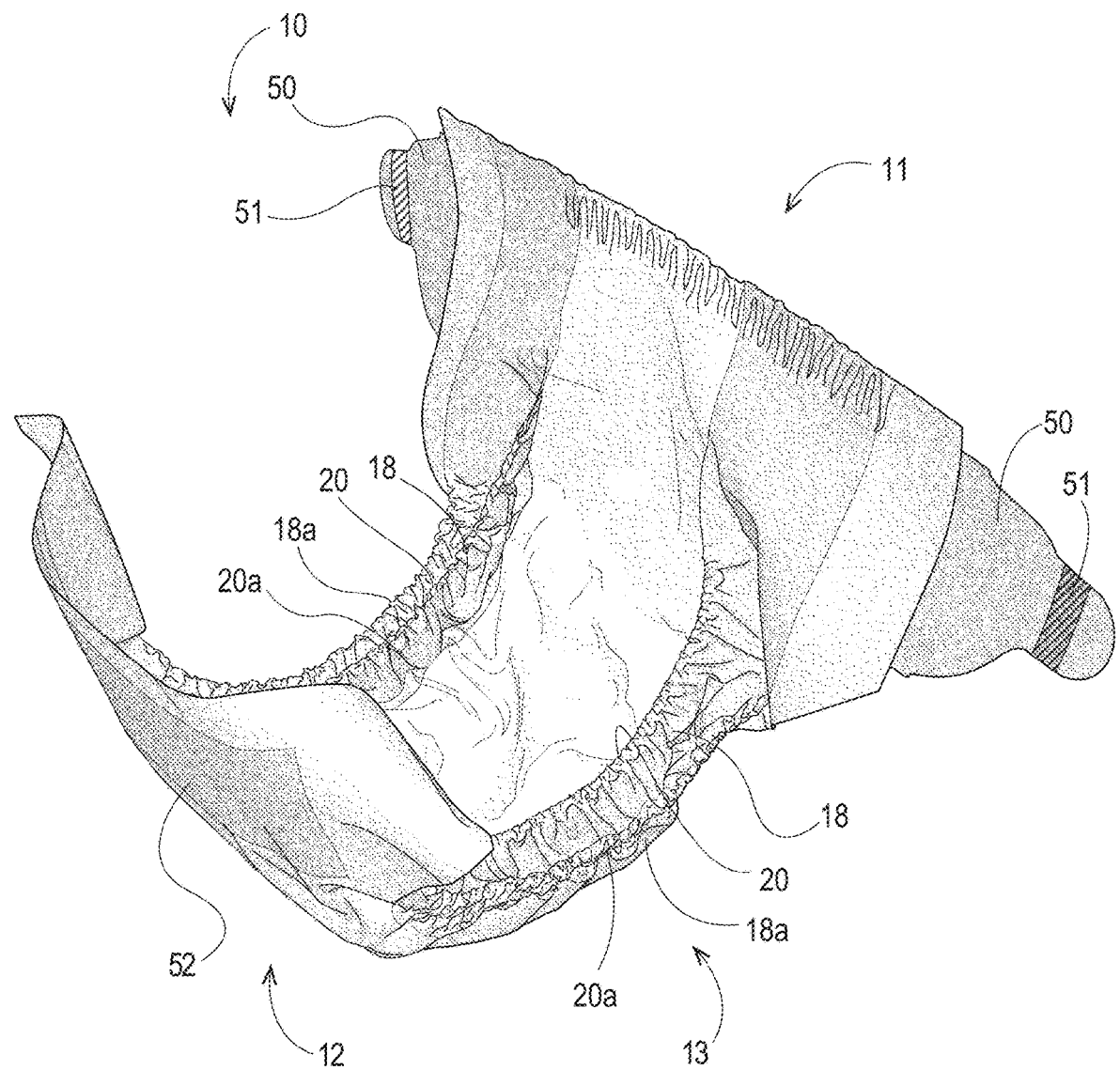
FIG. 9 is a perspective view of a diaper in a relaxed, opened position as it might appear resting on a table, wearing-facing side up.
Figure 10A:
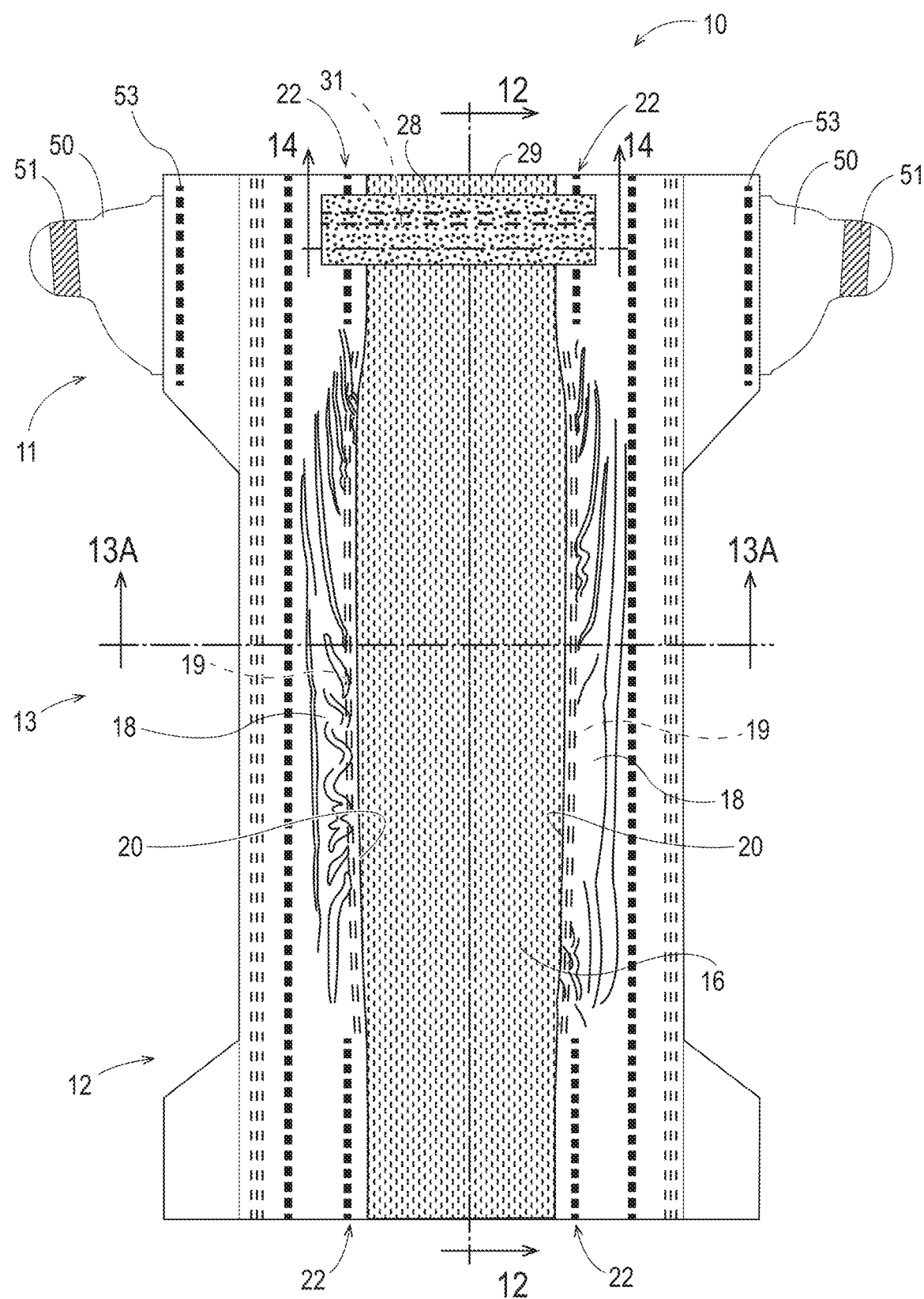
FIG. 10A is a plan view of a diaper in an extended and flat condition, with wearer-facing surfaces facing the viewer.
Figure 10B:
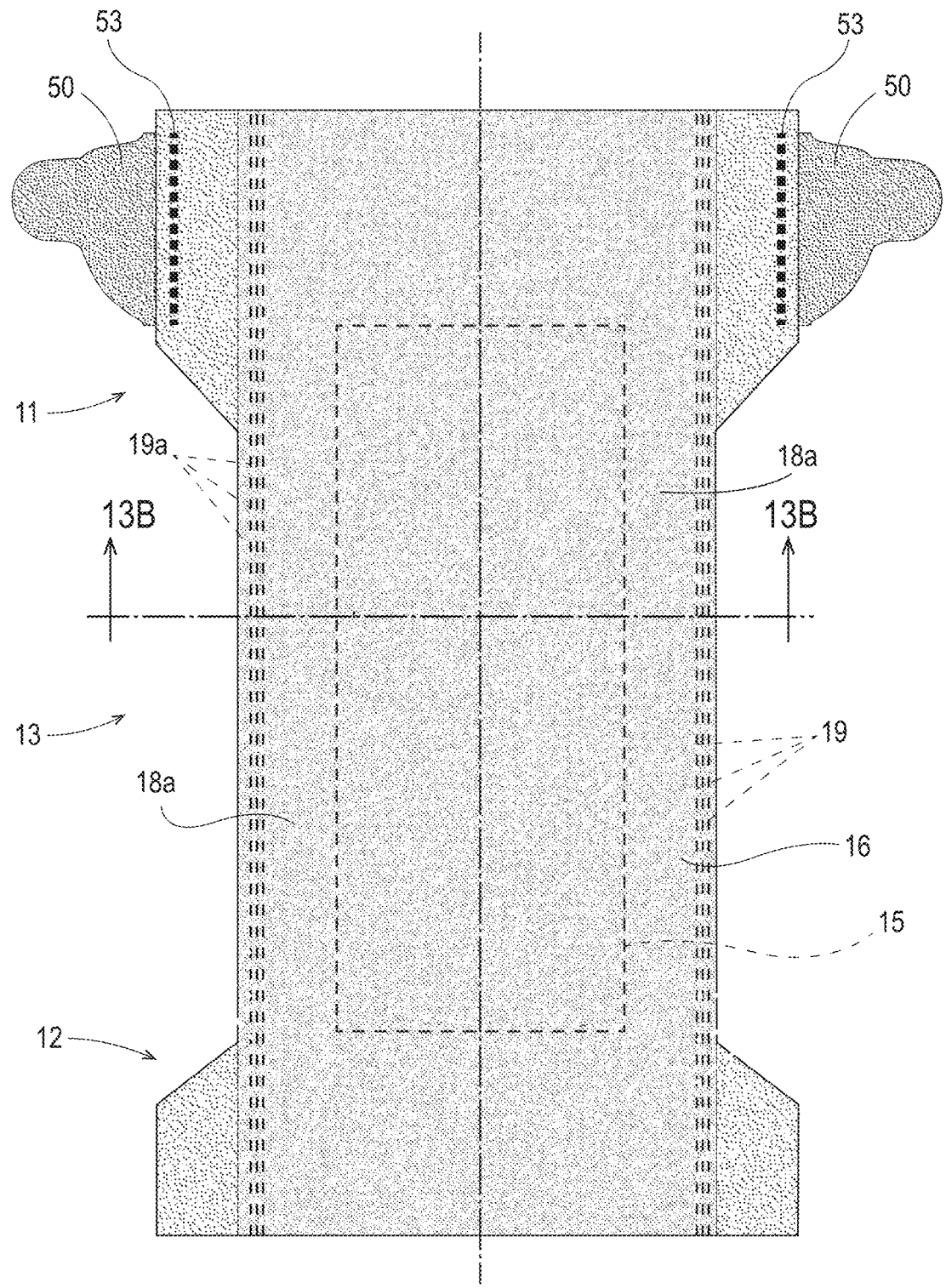
FIG. 10B is a plan view of another example of a diaper in an extended and flat condition, with wearer-facing surfaces facing the viewer.
Figure 11:
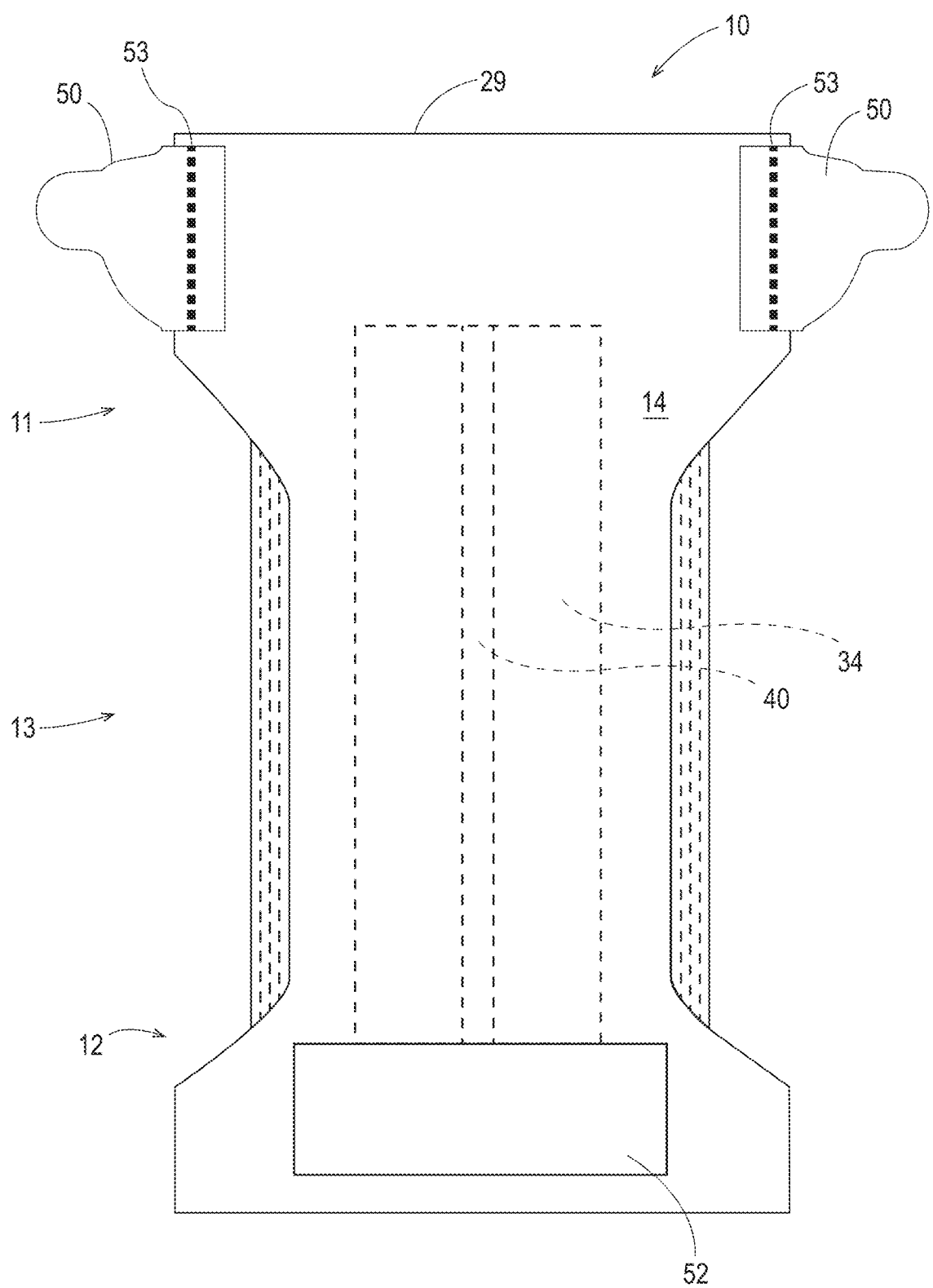
FIG. 11 is a plan view of a diaper in an extended and flat condition, with outward-facing surfaces facing the viewer.

As may be appreciated from FIGS. 2A and 10A, the material forming longitudinal cuffs 18 and the free distal edges 20 thereof may additionally be bonded to the diaper structure at cuff edge/end bonds 22. In combination, cuffs 18 may each include one or more longitudinal cuff elastic members 19 proximate the free longitudinal distal edges 20. During manufacturing, longitudinal cuff elastic members 19 may be incorporated and affixed into the cuff 18 structures in a pre-strained condition. Upon completion of manufacturing, release from the manufacturing line, and relaxation of the diaper structure, the elastic members 19 longitudinally contract toward their unstrained lengths, causing the free edges 20 to pull longitudinally against the cuff end/edge bonds 22, thereby causing the diaper 10 structure to curl toward the wearer-facing side as suggested in FIGS. 1 and 9, and causing the free edges 20 of the cuffs to pull away from the structure and the cuffs to "stand." This feature causes the free edges 20 of the cuffs to extend toward and draw against the wearer's skin along the buttocks and through the crotch region, when the diaper is worn, thereby performing a gasketing function that serves to contain exudates between the cuffs 18.

This combination of cuff end/edge bonds 22 and prestrained longitudinal cuff elastic members 19 can cause the cuffs 18 to stand as described above regardless of whether the edges 20 and end/edge bonds 22 are disposed inboard, or outboard, of the affixed proximal portions 21 of the cuffs. In the examples depicted in FIGS. 2A, 2B, 4, 5, 10A and 13A, it can be appreciated that the location of end/edge bonds 22 relative affixed proximal portions 21 causes the free edges 20 of cuffs 18, while standing, to be drawn by contraction of elastic members 19 toward the center of the diaper (i.e., toward longitudinal axis 4-4). This may cause free edges 20 to tend to rest against areas of the wearer's crotch region closer to the longitudinal center of the diaper when the diaper is worn. In another example, however, cuffs 18 may be constructed such that end/edge bonds 22 are disposed outboard of the affixed proximal portions of the cuffs 18, such that free edges 20 of cuffs 18 are drawn by contraction of elastic members 19 away from the longitudinal axis 4-4, i.e., toward more outboard regions of the diaper. This may cause free edges 20 of cuffs 18 to tend to rest against the wearer's skin in locations more laterally removed from central areas in the wearer's crotch region, e.g., against the inward-facing surfaces of the buttocks in the gluteal cleft, and against the inner thighs in the crotch region. Better gasketing and better liquid containment may occur with one or the other configuration depending upon wearer size, position and activity level, and thus one or the other configuration may be preferred under given circumstances. Other non-limiting examples of suitable longitudinal cuff construction are described in U.S. Pat. No. 7,794,441.

Elastic members 19 may be discontinuously or continuously adhered along their lengths to the material(s) forming cuff 18 structures by, e.g., adhesive applied by strand-coating the elastic members. In some examples the material forming the cuffs 18 may be folded over the elastic members 19 to better contain them and restrain them within the cuff structure in the event of failure of the adhesive. This has the further advantage of providing a folded (rather than cut) material edge as distal edge 20, providing a neat appearance and softer feel.

In some examples it may be desired that rear topsheet 16r and longitudinal cuffs 18 are continuously integrally joined where they meet, thereby preventing escape of liquid at the junction therebetween. In one example suggested in FIG. 6A, an effectively liquid impervious sheet or web material (such as a polymer film) forming rear topsheet 16r in whole or in part may contiguously form a portion or layer of each longitudinal cuff 18 in the rear portion of the diaper. In one example, an effectively liquid impermeable sheet or web material (such as a polymer film) forming topsheet 16, 16f and or 16f in whole or in part may contiguously form a portion or layer of each longitudinal cuff 18. The impermeable topsheet material can be imparted with a pattern of apertures to render it liquid permeable in a zone or region overlying an absorbent core and/or liquid control structure 15.

In simplified examples made more apparent in FIGS. 7, 8, 10B and 13B, longitudinal outer cuffs 18a may be formed by an alternative and/or additional configuration by portion(s) of the material of the topsheet 16, 16f, 16r and/or backsheet 14 extending laterally beyond the liquid control structure 15, with attached, sandwiched, enveloped or otherwise captured outer cuff elastic members 19a. Outer cuff elastic members 19a may also be incorporated into the structure while in a pre-strained condition as described above. Upon completion of manufacturing, release from the manufacturing line, and relaxation of the diaper structure, the elastic members 19a longitudinally contract toward their unstrained lengths, causing the free edges 20a to pull longitudinally, thereby causing the diaper 10 structure to curl toward the wearer-facing side as suggested in FIGS. 1 and 9, and causing the free edges 20a of the cuffs to lift up from the structure and the outer cuffs to "stand". This feature causes the free edges 20a of the outer cuffs to draw against the wearer's skin along the inner thighs and buttocks, when the diaper is worn, thereby performing a gasketing function that serves to contain exudates within the diaper.

In another example apparent in FIGS. 1, 2A, 5, 6A, 9, 10A and 13A, a diaper may be configured with two pairs of longitudinal cuffs, longitudinal cuffs 18, and outer longitudinal outer cuffs 18a.

Exudates Indicator

It may be desired that the diaper 10 include a wetness indicator 40 (see, e.g., FIGS. 3A-6A and 11-13B) that imparts a visible change of appearance to the diaper on the outside, when liquid exudate(s) has (have) entered the space containing the absorbent core and/or liquid control structure. This can help notify the caregiver that a discharge of exudate(s) has occurred, and thereby promote a prompt removal of the diaper from the patient to, for example, reduce the chances that the infant's skin will be irritated by exudates, that a stool sample will be contaminated by urine that may escape into the space in the rear portion adapted for receiving the stool sample (or vice versa), and/or facilitate prompt sample collection.

The wetness indicator may have any form, composition or configuration suitable for a relatively prompt response. In one example, a wetness indicator may include a material applied or affixed to the wearer-facing surface of the backsheet 14, in the envelope space between the topsheet and the backsheet where exudate will be received. In another example, a wetness indicator may include an indicator material applied or affixed to an outward-facing surface of the liquid control structure 15 and/or liquid control structure 35. The indicator material may include a composition selected, formulated and/or adapted to visibly change appearance when wetted, or when warmed by contact with recently discharged exudate. The appearance change may be one or more of a change in color, an appearance or disappearance of a visible element, or any other visible change that occurs when the composition is wetted or warmed. The material(s) forming liquid impermeable backsheet 14 may be selected to have sufficient translucence (e.g., sufficiently low opacity) to enable effectively clear visibility of the wetness indicator on the outside of the diaper, in combination with the materials, composition, configuration and placement location of the wetness indicator 40. Non-limiting suitable examples are described in U.S. provisional application Ser. Nos. 62/147,258 and 62/186406. Other non-limiting suitable examples are described in U.S. Pat. Nos. 8,927,801; 8,618,349; 7,332,642; 7,159,532; 6,075,178; and 4,231,370; and U.S. published application nos. 2015/173968; 2013/116644; 2011/137274; and 2004/0254549.

In other examples, an included wetness indicator may operate to electrically/electronically trigger a visible and/or audible signal when the diaper is wetted. In some examples, a combination of a sensing device or devices included in components of the diaper that will be exposed to wetness, and a signal-receiving/processing device, may be included. In such examples, the sensing device in the diaper generates a signal indicative of a wetted condition, and the signal-receiving/processing device receives the signal and provides a visible and/or audible signal to the caregiver. In some examples, the signal-receiving/processing device may be remote from the diaper and may be carried about by the caregiver. Non-limiting examples are described in U.S. Pat. Nos. 9,241,839 and 6,603,403; and U.S. Pat. App. Pub. Nos. 2010/0030173 and 2010/0164733. Various improvements and variations of such examples as well as other configurations of diaper wetness detection devices are described and known in the art.

In still other examples, it may be desired that the diaper include a device adapted to detect, and cause generation of a visible and/or audible signal of, the presence of stool in the diaper. This may provide another means of facilitating the prompt retrieval of an unadulterated stool sample. Non-limiting examples are described in U.S. Pat. No. 8,933,292.

Examples of Features for Stool Sample Collection

FIGS. 1-8 depict various features that may be embodied in a diaper 10. Diaper 10 may have a rear portion 11, front portion 12 and perineal portion 13 between the front portion and rear portion. For reference, the lateral width of diaper 10 may be equally divided by an imaginary longitudinal axis 4-4 (FIG. 2A).

Front and Rear Topsheets

Diaper 10 may include a liquid control structure 15 adapted to receive, absorb and retain liquid exudates (e.g., urine). As may be seen in FIGS. 4A-6, liquid control structure 15 may be disposed in the diaper between backsheet 14, and a front topsheet 16f in the front portion 12, and a rear topsheet 16r in the rear portion 11.

The front topsheet 16f may be formed of a liquid permeable material, for example, a nonwoven material such as described in U.S. Pat. No. 8,968,614. For purposes of ensuring rapid passage of urine through the front topsheet 16f to the materials of the liquid control structure 15, thereby minimizing chances of contamination of a stool sample with urine, it may be desired that the front topsheet 16f be formed of an apertured nonwoven material formed of fibers. The fiber constituents may be selected or manufactured to be inherently hydrophilic, or may be treated, e.g., with an application of a surfactant, to impart hydrophilic surface properties. Suitable examples of apertured topsheets are described in U.S. Pat. Nos. 7,033,340; 6,680,422; 6,498,284; 6,414,215; 5,516,572; and 5,342,338; and in pending U.S. application Ser. No. 14/270,468.

The rear topsheet 16r may be formed of an effectively liquid impermeable material that hinders or blocks passage of liquid constituents therethrough. In one example, rear topsheet 16r may be formed of a polymeric film. In another example, rear topsheet 16r may be formed of an effectively liquid impermeable nonwoven web material. An example of such material is disclosed in, for example, U.S. Pat. App. Pub. No. 2006/0014460.

For purposes of simplification of manufacturing, it may be desired that the material forming a liquid permeable front topsheet 16f extends to the rear portion of the diaper, or even the full length of the diaper 10. This eliminates the need for special cutting and/or material bonding steps that would be associated with including a foreshortened front topsheet 16f, i.e., one that does not extend the full length of the diaper. If a full-length front topsheet 16f is included, it may be simply overlaid by the effectively liquid-impermeable rear topsheet 16r.

In another example, one contiguous sheet of material may be used to form both front topsheet 16f and rear topsheet 16r. The material may manufactured or treated to be effectively liquid permeable in the front portion 12 and effectively liquid impermeable in the rear portion 11. In one particular example, an effectively liquid impermeable material may form a single contiguous layer constituting both front topsheet 16f and rear topsheet 16r, but the material may be subjected to an aperturing process that forms apertures in the front portion, making the front topsheet 16f portion effectively liquid permeable. In another particular example, an effectively liquid permeable material may form a single contiguous layer constituting both front topsheet 16f and rear topsheet 16r, but the material may be subjected to a process rendering it effectively liquid impermeable in the rear portion. Suitable processes may include applying a film layer to the rear portion; applying a melted hydrophilic polymer composition to the rear portion by methods such as slot coating or roller techniques such as used in printing; spraying a hydrophilic coating material (such as, for example, a wax) over the material of the rear portion, etc.

In another simpler example, the rear topsheet 16r and the backsheet 14 may be integral and/or unitary in the rear portion of the diaper, behind the transverse perineal barrier 23 (described below). In other words, a single, effectively liquid impermeable web member or a single, effectively liquid impermeable multi-layer laminate, may form both the outward-facing surface of the diaper and the wearer-facing surface of the diaper, in the rear portion of the diaper, with no separate intermediate layer. In such example, the components of the liquid control structure may be disposed only in the portion of the diaper forward of the transverse perineal barrier 23. This example is illustrated schematically in FIG. 4B.

Pass-Through Port and Stool Sample Receptacle

It may be appreciated that a close-fitting diaper may have limited volume available in the rear region for receipt, containment and non-absorptive storage of discharged stool prior to the time the diaper is removed for sample retrieval. In some circumstances it may be expected that the infant patient may discharge a volume of stool that is larger than a close-fitting diaper has capacity to receive and contain. In some circumstances it may be desired that the discharged stool contact the infant patient's skin as little as possible. In such circumstances and others, it may be desired that the diaper be imparted with a structure providing greater volume capacity.

Thus, referring to FIGS. 2B, 3B, 4C, 4D and 6B, in some examples, the diaper may be provided with a pass-through port 60, positioned generally in the perineal portion or crotch region 13 and/or the rear portion or rear region 11 of the diaper, proximate the expected wearer's anus, which will allow stool exudate to pass entirely through the diaper to the outside thereof. The pass-through port 60 may be accompanied by a sample collection receptacle 61, suitably sealingly affixed about the perimeter of the port 60 so as to prevent leakage of stool exudate out of the diaper. Collection receptacle 61 may have any suitable form, structure and composition. In some examples, collection receptacle 61 may be a bag structure, having an open end and a closed end, formed of liquid impermeable polymeric film. In some examples receptacle 61 may be provided with a rolled, folded, pleated or similar configuration, and/or stretch capability, that allows it to expand and/or increase in containment volume with a discharge of exudate thereinto. The diaper may be provided initially (i.e., as packaged) with the receptacle in a substantially collapsed condition, such that its available containment volume is not occupied by air. The collapsed condition may be enabled by a configuration of rolling, folds, pleats, contracted state of the material of which the receptacle is formed, etc. In other examples the receptacle may be releasably held in a collapsed condition against surrounding portions of the diaper by a releasable mechanism such as a patch of releasable adhesive, a hook-and-loop system, a releasable tape, etc. When a volume of air is not initially present within the receptacle that must be to be displaced to receive stool by pressure from a discharge thereof, the receptacle's receipt and acceptance of a discharge may be eased.

In some examples, the edges of a suitable bag structure about its open end may be sealingly affixed by adhesive or other suitable mechanism about the perimeter of port 61, to the wearer-facing surface and/or to the outward-facing surface of a liquid impermeable rear topsheet 16r. Similarly, the edges of backsheet material about the port 61 may be directly or indirectly sealingly affixed to the outside surfaces of the receptacle 61. To facilitate sealing about port 60, receptacle 61 may include a sealing flange 62, which may be used to sealingly affix receptacle 61 to the diaper. In the non-limiting examples shown, sealing flange 62 is sealingly affixed to the rear topsheet 15r of the diaper about port 60, however, other configurations are possible.

The receptacle 61 may be formed of a material containing or including substantially no substances that will dissolve or otherwise intermix with fecal matter, thereby reducing the potential for contamination of the sample. In some examples, the receptacle 61 may be formed of a polyolefin film, for example, polyethylene.

Figure 4A:
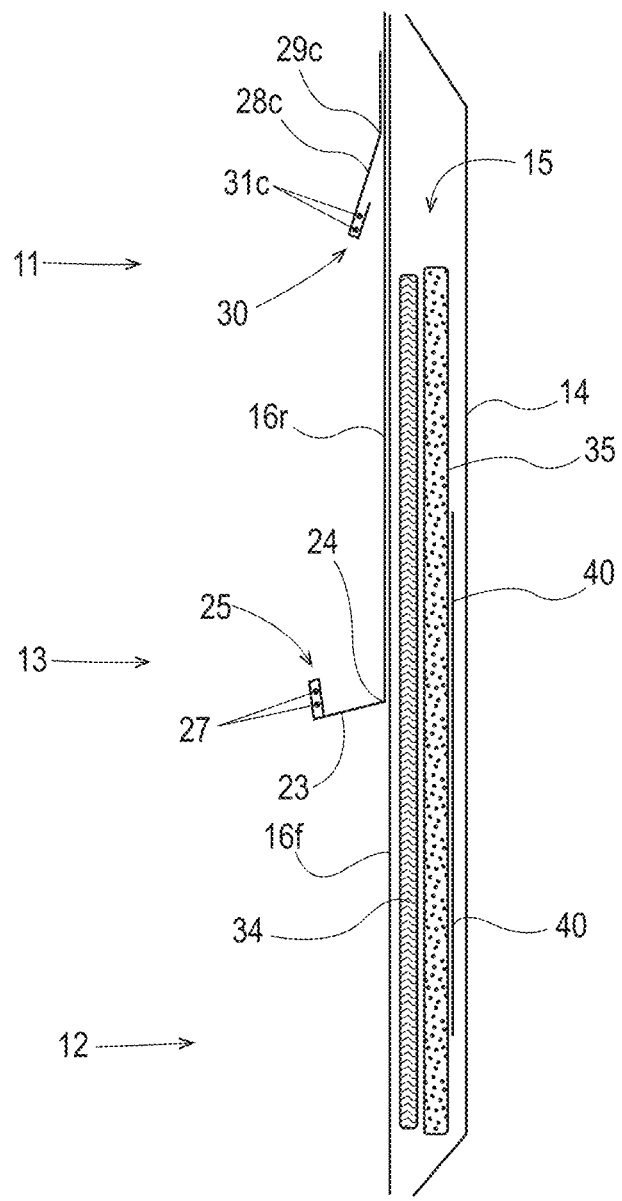
FIG. 4A is a schematic, exploded longitudinal cross-section of one example of a diaper as shown in FIG. 2A, taken along line 4-4 shown in FIG. 2A.
Figure 4B:
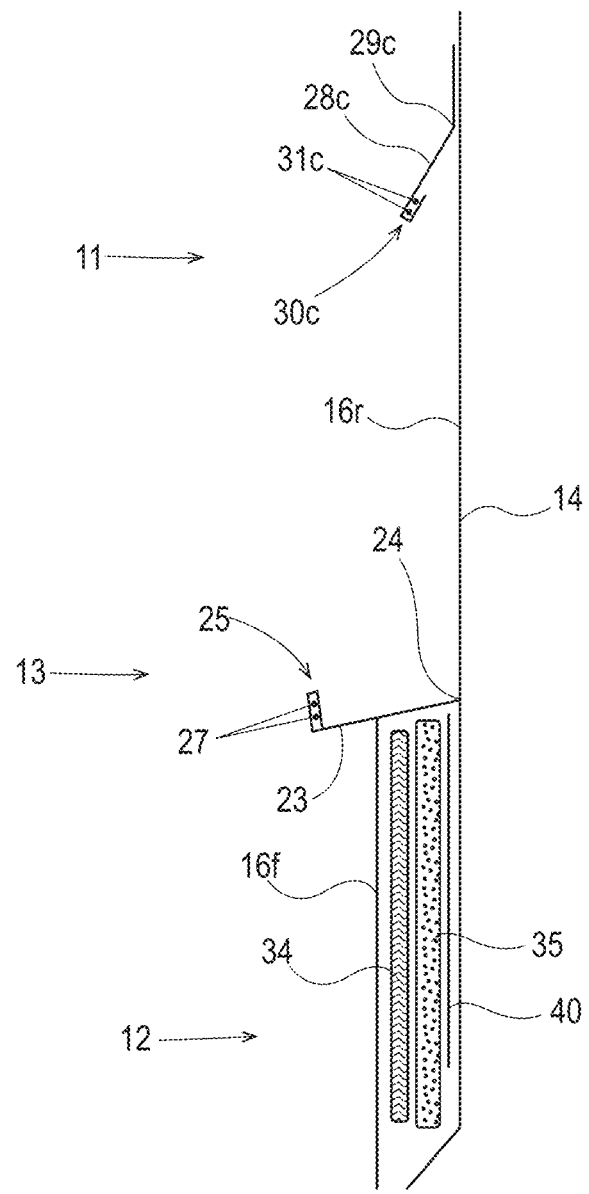
FIG. 4B is a schematic, exploded longitudinal cross-section of another example of a diaper as shown in FIG. 2A, taken along line 4-4 shown in FIG. 2A.
Figure 4C:
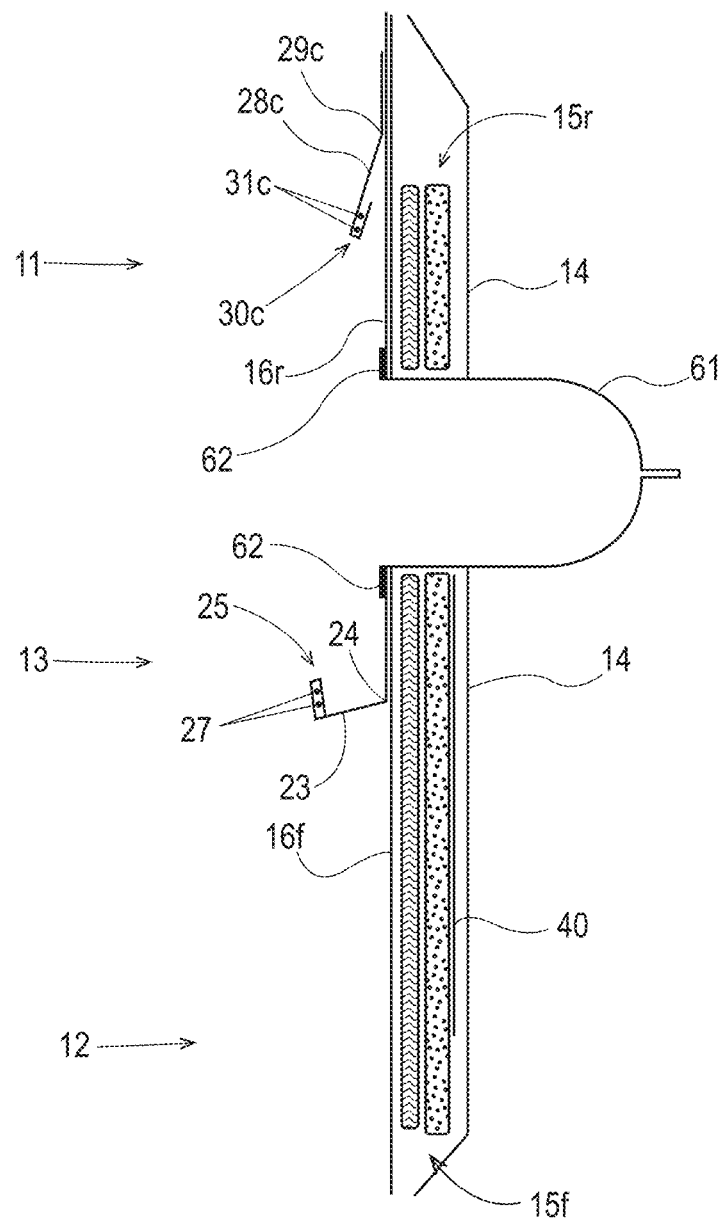
FIG. 4C is a schematic, exploded longitudinal cross-section of one example of a diaper as shown in FIG. 2B, taken along line 4-4 shown in FIG. 2B.
Figure 4D:
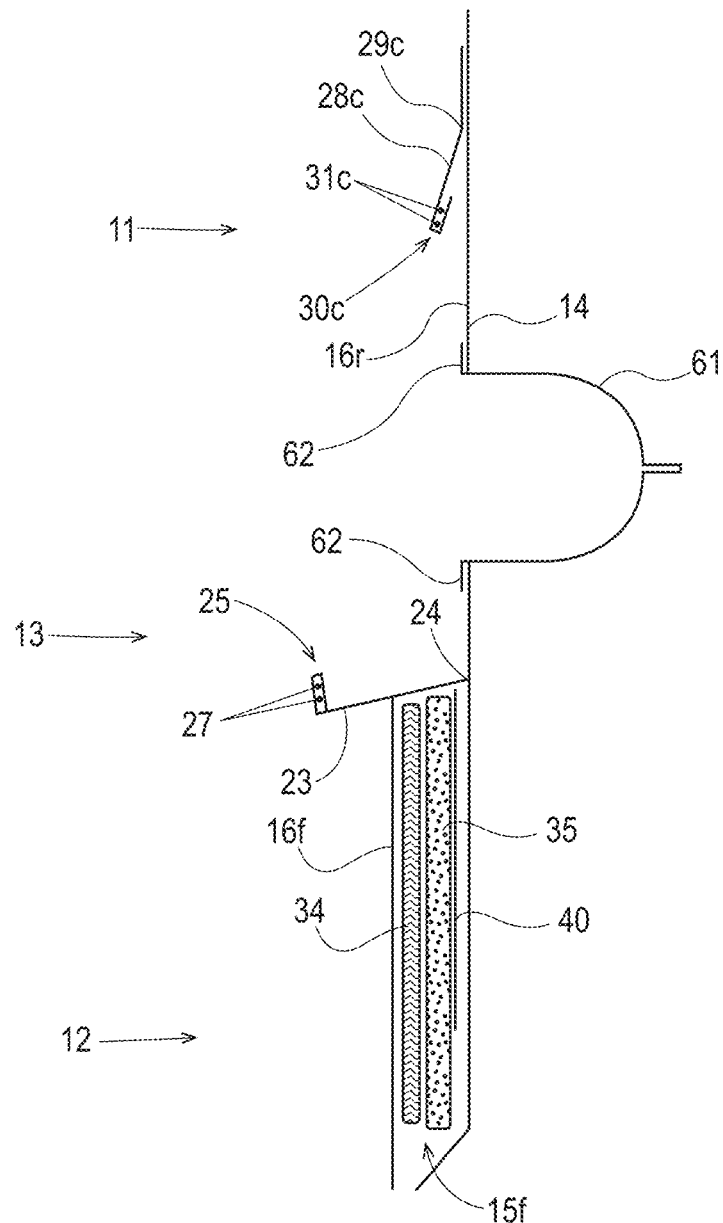
FIG. 4D is a schematic, exploded longitudinal cross-section of another example of a diaper as shown in FIG. 2B, taken along line 4-4 shown in FIG. 2B.
Figure 4E:
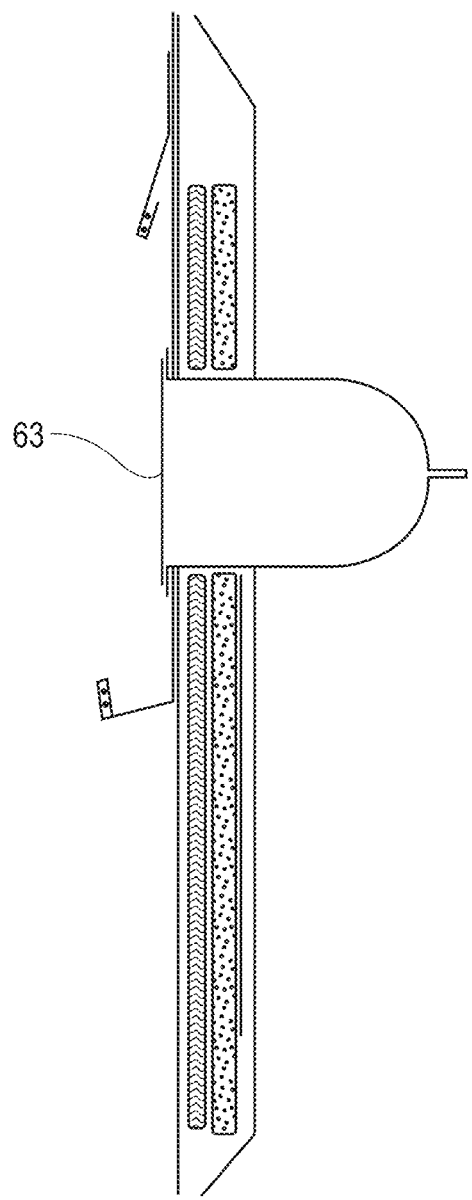
FIG. 4E is a schematic, exploded longitudinal cross-section of another example of a diaper as shown in FIG. 2B, taken along line 4-4 shown in FIG. 2B.
Figure 5:
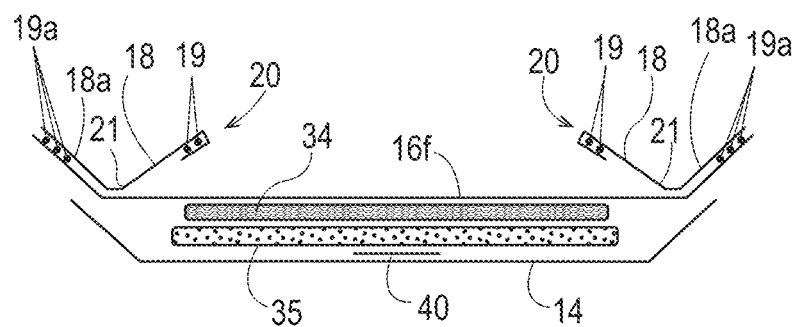
FIG. 5 is a schematic, exploded lateral cross-section of one example of a diaper as shown in FIG. 2, taken along line 5-5 shown in FIG. 2A.
Figure 6A:
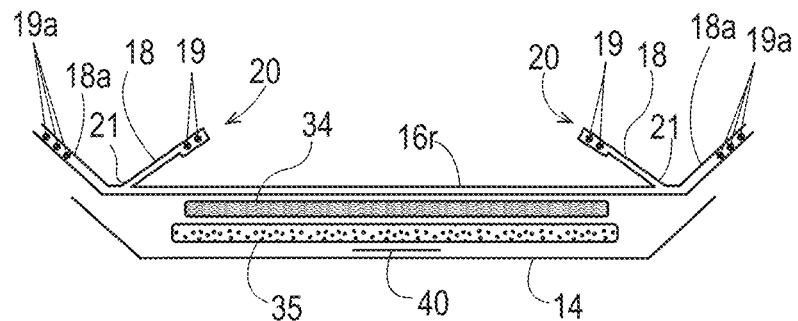
FIG. 6A is a schematic, exploded lateral cross-section of one example of a diaper as shown in FIG. 2A, taken along line 6-6 shown in FIG. 2A.
Figure 6B:
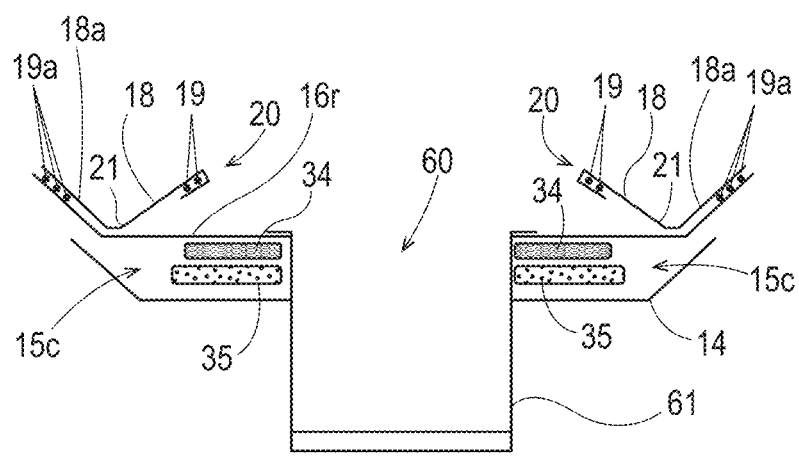
FIG. 6B is a schematic, exploded lateral cross-section of another example of a diaper as shown in FIG. 2B, taken along line 6-6 shown in FIG. 2B.
Figure 7:
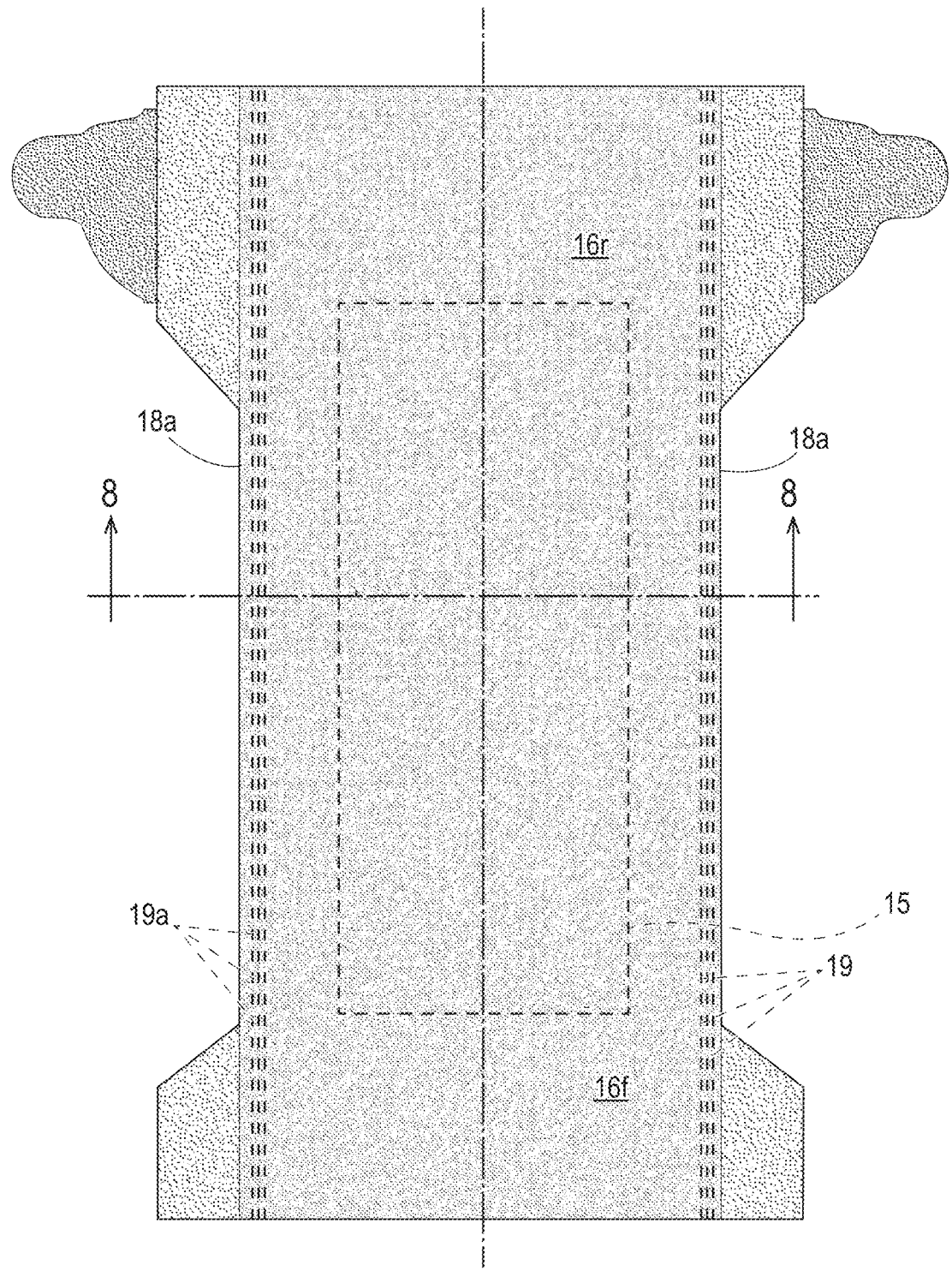
FIG. 7 is a plan view of another example of a diaper in an extended and flat condition, with the wearer-facing surfaces facing the viewer.
Figure 8:
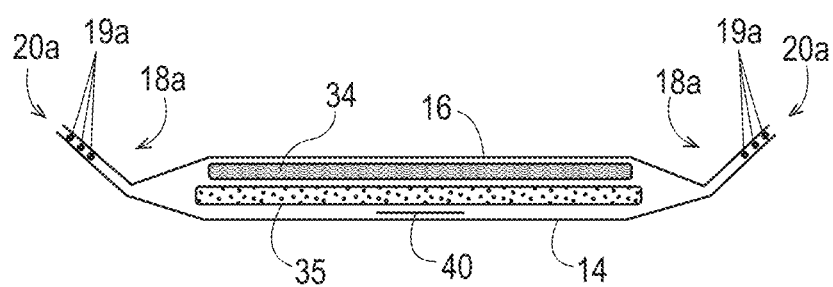
FIG. 8 is a schematic, exploded lateral cross-section of a diaper as shown in FIG. 7, taken along line 8-8 shown in FIG. 7.

In some examples, the receptacle 61 may be deemed a continuation and/or extension of a liquid impermeable topsheet 16r (such as suggested in FIGS. 4C and 6B). In some examples, the receptacle 61 may be deemed a continuation and/or extension of a liquid impermeable backsheet 14 (such as suggested in FIG. 4D), where the rear topsheet 16r and the backsheet 14 are essentially the same sheet/web component. In some examples a single, unitary sheet or section of polymer film may be formed to constitute the liquid impermeable rear topsheet 16r and the receptacle 61 as a continuous structure, wherein the rear topsheet 16r and receptacle 61 are integral.

The volume capacity of the receptacle is reflected by the liquid holding capacity of the portion of the receptacle, disposed below a horizontal x-y plane occupied by the topsheet stretched out horizontally against contraction induced by elastic members included in the diaper, to the fullest non-deformed dimensions of the non-elastic materials of the diaper, with the liquid at ambient pressure. For a receptacle positioned to receive stool discharge (i.e., with its center to the rear of a lateral axis equally dividing the length of the diaper), it may be desired that the receptacle have a liquid holding capacity of least about 5 ml, more preferably at least 10 ml, 25 ml or even 50 ml.

Referring to FIGS. 4E and 19A-E, the diaper also may be provided with a stool gate 63 that will admit discharged stool into the receptacle 61 and help retain the stool within the receptacle following discharge. In some examples gate 63 may be formed of or include a sheet of polymer film or other suitable sheet material, and be disposed over and/or across pass-through port 60 or otherwise over, across and/or in front of the wearer-facing end of receptacle 61. It may be desired that the material(s) used to form gate 63 be hydrophobic, or be treated to be hydrophobic, so that discharged stool is less likely to adhere to it and will more easily pass along the surfaces thereof. The sheet of film or other sheet material may have a gate entry 64 therethrough, which will allow stool to pass therethrough into receptacle 61. In some examples gate entry 64 may be a slit, aperture or orifice through the sheet of film or other sheet material. In examples illustrated in FIGS. 19B, 19C and 19E gate entry 64 may include a curved slit through the sheet material, or a configuration of line segments of slits through the sheet material, that are configured to form flexible flaps 65 and/or otherwise allow the sheet material thereabout to flex so as to create an adjustably-sized opening as a result of contact with and pressure thereagainst by a stool discharge. If the selected sheet material is substantially elastic/resilient, the flexible flaps will substantially return to their original positions, reclosing gate entry 64 after stool passes therethrough. A stool gate 63 may be included to help isolate discharged stool from contact with the wearer's skin, and help reduce chances of contamination by urine, following discharge.

When the receptacle 61 is a bag structure, e.g., formed of a polymeric film, upon a discharge of stool thereinto by an infant-patient, the caregiver may collect the sample by separating the bag from the diaper by, e.g., cutting it away, e.g., with a pair of scissors. This enables the caregiver to remove the sample without immediately removing the diaper from the infant, facilitating neater sample collection. In other examples, the receptacle may be provided with features that make it detachable about a perimeter proximate the perimeter of the pass-through port 60. In one particular example, the receptacle may be provided with a line or path of perforations or scoring (not shown) about its perimeter proximate the perimeter of the port 60. To prevent leakage, the perforations or scoring may be covered with a removable adhesive strip (e.g. adhesive tape) (not shown) covering the perforations or scoring. Following a discharge of stool the caregiver may remove the strip/tape, and tear the receptacle bag away from the diaper, along the line or path of perforations or scoring, and thereby collect the sample. In other examples, an adhesive used to sealingly affix the receptacle to the portions of the diaper surrounding the port 60 may be a releasable adhesive, such that it will release its grip on the material of the receptacle with relatively modest application of tugging, pulling or peeling force exerted by the caregiver. In other examples, the receptacle may be affixed to the diaper by frangible mechanical and/or thermal bonds which may be relatively easily broken and separated by the caregiver via modest application of force.

In some examples, the receptacle may be provided with its own sample release port (not shown), valve or opening therein, at a location removed from that of pass-through port 60. The diaper may be initially provided with a removable covering (not shown) or sticker over a sample release port or opening in the receptacle bag. Upon a discharge of stool, the caregiver may remove the covering and to expel the contents of the receptacle through the release port or opening, into a sample container. In another example, the bag may be held sealingly closed at a distal end by an openable mechanism (not shown) such as, or having cooperating features structurally similar to, any of a variety of ZIPLOC—(trademark of S.C. Johnson & Son, Inc., Racine, WS) type bag closure devices. Following a discharge of stool into the receptacle, the device may be opened to empty a stool sample contained in the receptacle, into a sample container.

It may also be desired that the material of which receptacle 61 is formed be substantially translucent such that a caregiver viewing it may readily visually detect whether the receptacle contains stool. Thus, it may be desired that the material of which the receptacle is formed have an opacity no greater than 50 percent, more preferably no greater than 45 percent, even more preferably no greater than 40 percent, and still more preferably no greater than 35 percent, as measured by the opacity test method described below.

Figure 3A:
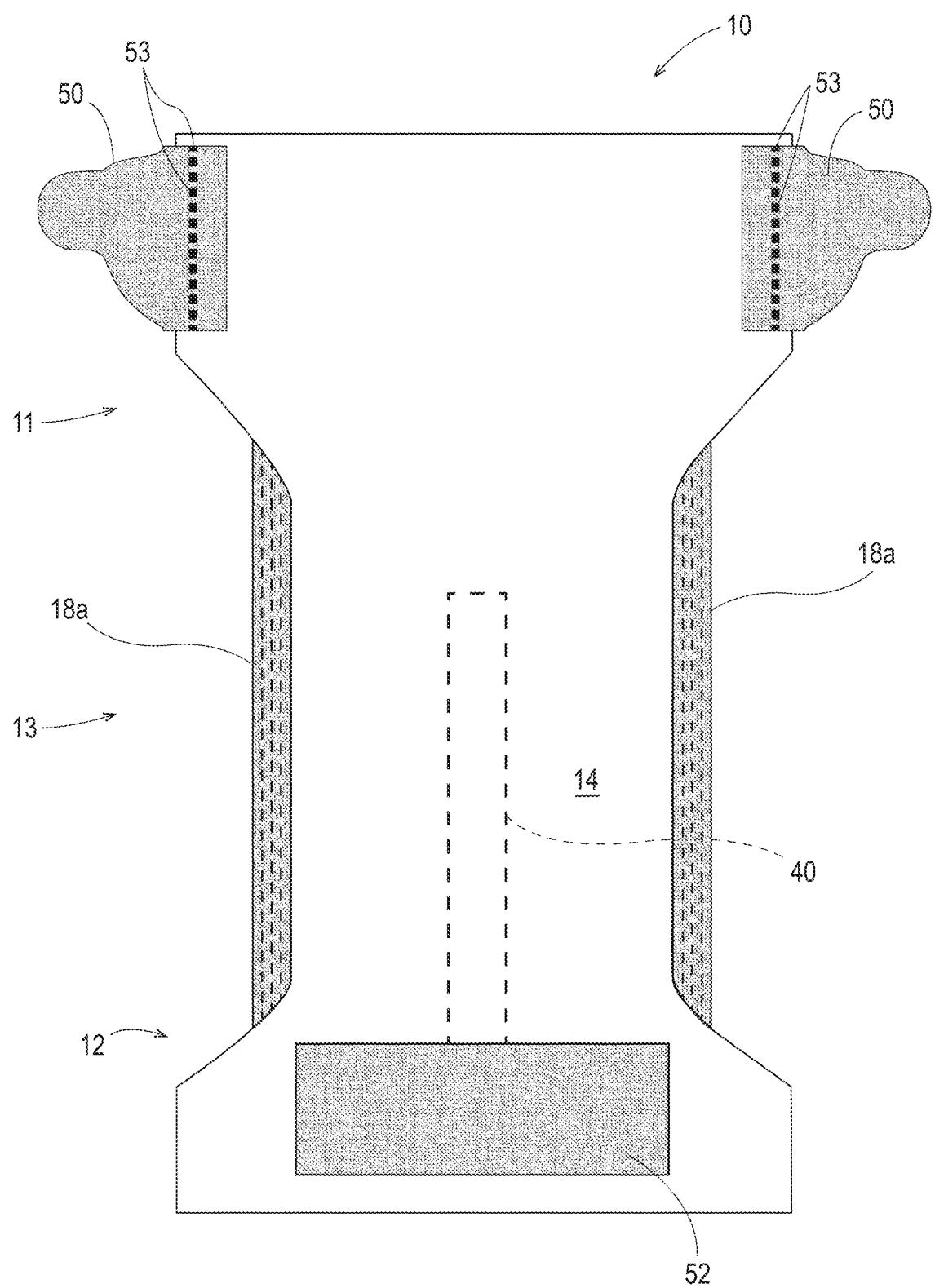
FIG. 3A is a plan view of a diaper in an extended and flat condition, with the outward-facing surfaces facing the viewer.
Figure 3B:
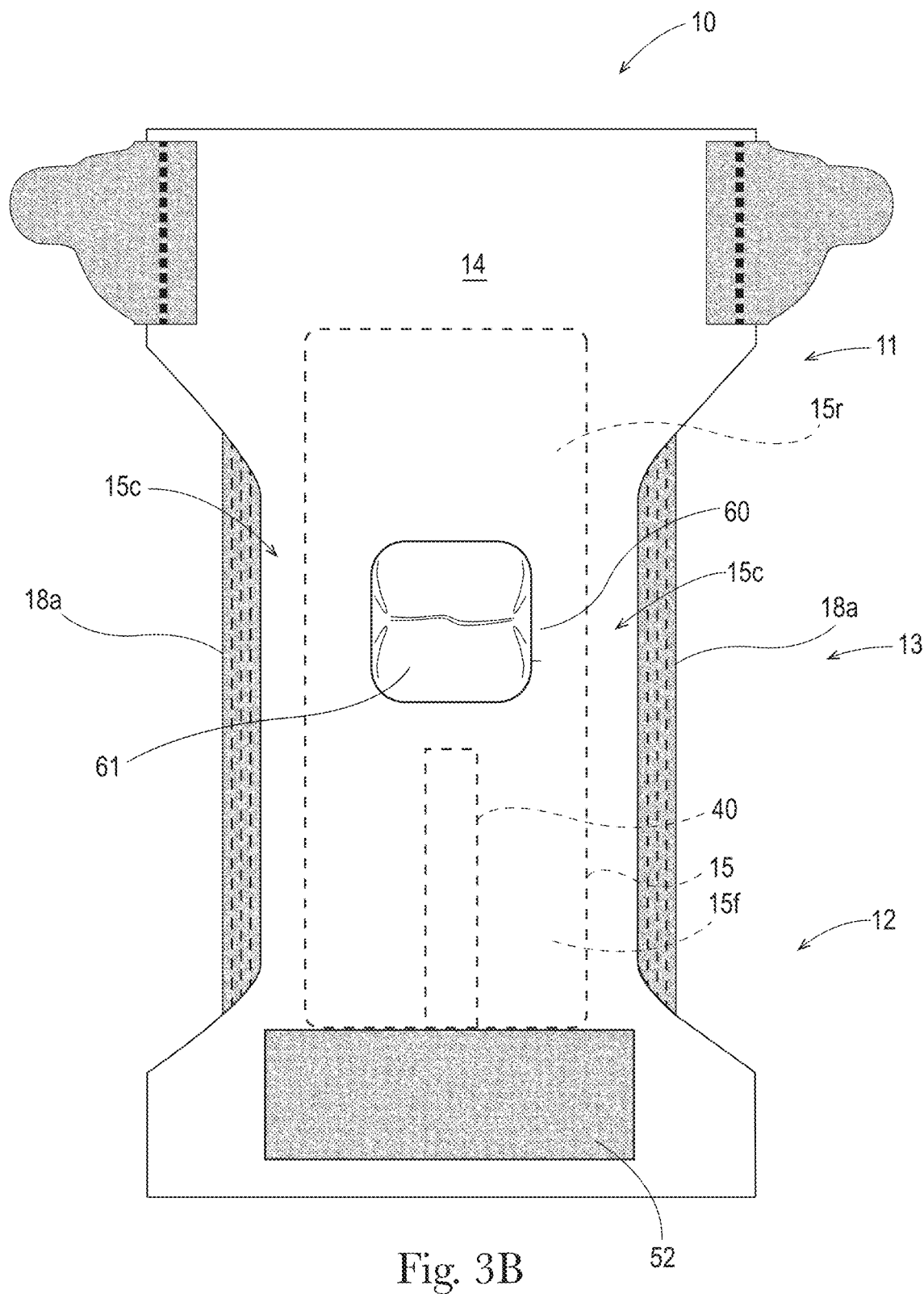
FIG. 3B is a plan view of another example of a diaper in an extended and flat condition, with the outward-facing surfaces facing the viewer.

It will be appreciated that, where a pass-through port 60 of any substantial size is included, the plan surface area within the perimeter of the port reduces the plan surface area of the space between the topsheet and backsheet that is available to be occupied by an liquid control structure 15, acquisition layer 34, absorbent layer 35, urine capture layer 34a, or combination thereof. Referring to FIGS. 3B and 4C, where a relatively larger urine storage capacity is required to minimize the chances that a stool sample will be contaminated by discharged urine, it may be desired that the diaper include both a front liquid control structure 15f and a rear liquid structure 15r, to provide the desired urine storage capacity. Where discharged urine is prevented from traveling to the rear of the diaper over the wearer-facing side of the topsheet by, e.g., a transverse perineal barrier 23, it may be desired that side passageways 15c are included to provide channels to enable fluid transport around port 60, between front and rear absorbent structures 15f, 15r (see FIGS. 3B and 6B). Side passageways 15c are portions of the enveloped space between the topsheet and backsheet, laterally outboard of the side edges of the port 60. Side passageways 15c may be open channels or voids, substantially free of any liquid control and/or absorbent materials, or may be occupied by urine capture layer material, acquisition layer material or absorbent layer material, or any combination thereof deemed suitable to provide for controlled fluid transport between regions forward of port 60 and rearward of port 60, within the envelope formed by the topsheet and backsheet. Thus, passageways 15c may allow urine to travel from the front of the diaper to the rear of the diaper, and be absorbed in rear liquid control structure 15r in the event the front liquid control structure has insufficient capacity. In some examples port 60 may simply be cut or punched through a liquid control structure, urine capture layer or absorbent core structure, leaving front, rear and side portions thereof intact and available to provide liquid transport and/or absorption functions, where the side portions occupy side passageways 15c.

In some examples it may be desirable to include a pass-through port and receptacle structure, as described above, toward the front of the diaper, i.e., forward of a lateral axis equally dividing the length of the diaper, for purposes of providing a volume of space to non-absorbably receive and retain urine discharged by the infant patient. Such a forward structure (not shown) may be positioned appropriately proximate the intended wearer's urethra/urine discharge location. Such a forward structure may have any of the features or any combination of the features described above, and may be provided in combination with, or as an alternative to, a rear port and receptacle structure, where an isolated volume and receptacle for non-absorbable receipt and retention of discharged urine may be desired.

Transverse Perineal Barrier

As reflected in FIGS. 1, 2A and 4A-4D, diaper 10 may include a transverse perineal barrier 23. Transverse perineal barrier 23 may be disposed in the perineal portion 13 of the diaper, suitably located to extend transversely across the diaper, between the anus and genitals of the wearer when the diaper is worn. A single diaper design may be manufactured with a transverse perineal barrier in a location suitable for both male and female wearers. Alternatively, a selection of at least two differing designs may be manufactured (and simultaneously offered for purchase, e.g., in an array), one for male wearers and one for female wearers. The two designs may differ in, at least, the location of the transverse perineal barrier, with one design having the perineal barrier in a location more closely suited to male wearer anatomy, and the other design having the perineal barrier in a location more closely suited to female wearer anatomy.

Transverse perineal barrier 23 may have a proximal portion 24 and a free distal edge 25. Free distal edge 25 of perineal barrier 23 may bridge respective free distal edges 20 of left and right standing longitudinal cuffs 18 or outer longitudinal cuffs 18a.

Transverse perineal barrier 23 may be formed of an effectively liquid impermeable material. In one example, it may be formed of a polymer film. In another example, it may be formed of an effectively liquid impermeable fibrous nonwoven web material, or a laminate of a polymer film and a fibrous nonwoven web material. In one example, perineal barrier 23 may be formed of the same type material as longitudinal cuffs 18.

Transverse perineal barrier 23 may be transversely affixed along the proximal portion 24 to an underlying component of the diaper structure by mechanical or thermal bonding, by adhesive or other means, or a combination thereof; however, use of adhesive to bond or supplementally bond proximal portion 24 to the structure may serve to provide a liquid seal at the junction between the barrier 23 and the underlying diaper structure. In one example, proximal portion 24 of the barrier 23 is bonded to the rear topsheet 16r with a continuous application of adhesive therebetween, to provide a liquid seal at the junction. The adhesive may be a hot-melt type adhesive conventionally used in the manufacture of disposable diapers.

In some examples it may be desired that rear topsheet 16r and perineal barrier 23 are continuously integrally joined where they meet, thereby preventing escape of liquid at the junction therebetween. In one example suggested in FIG. 4A, an effectively liquid impervious sheet or web material (such as a polymer film) forming rear topsheet 16r in whole or in part may contiguously form a portion or layer of perineal barrier 23. It may also be desired that side edges 26 of perineal barrier 23 are continuously integrally joined to the material forming longitudinal cuffs 18, thereby preventing escape of liquid at a junction therebetween.

Transverse perineal barrier 23 may be manufactured to have a substantially straight free distal edge 25 and may also include one or more perineal barrier elastic members 27. In a manner similar to inclusion of longitudinal cuff elastic members 19, during manufacturing, perineal barrier elastic members 27 may be incorporated and affixed into the barrier 23 structure in a pre-strained condition. Upon completion of manufacturing, release from the manufacturing line, and relaxation of the diaper structure, the elastic members 27 contract toward their unstrained lengths, causing the free distal edge 25 of barrier 23 to pull transversely against the respective free distal edges 20 of the longitudinal cuffs. When the longitudinal cuffs 18 "stand" as described above, this causes the perineal barrier 23 also to "stand". This feature causes the free distal edge 25 of the perineal barrier 23 to draw toward the wearer's skin across the perineum, when the diaper is worn, thereby performing a gasketing function that serves to prevent passage of liquid exudates between the cuffs 18 from the rear portion of the diaper 11 to the front portion of the diaper 12, and vice versa. Thus, urine exudate in the front of the diaper may be prevented from contaminating stool exudate contained in the rear portion of the diaper, and liquid constituent of stool exudate may be prevented from moving to the front portion 12 of the diaper where it could pass through a liquid permeable front topsheet 16f into the liquid control structure.

As suggested in FIGS. 4A and 4B, the transverse perineal barrier 23 may be configured such that a marginal portion proximate to distal edge 25 tends to bend over, which will cause it lay in a flat configuration against the wearer's skin when the diaper is worn. This may improve comfort of the diaper and reduce any tendency of the transverse barrier to chafe or mark the wearer's skin. In one example, elastic members 27 may be one or more flattened strips of elastomeric material (rather than round strands), which may further enhance the tendency of the marginal portion to bend and lay over flat against the wearer's skin. In one example, the marginal portion at left and right sides thereof may be attached to longitudinal cuffs along a direction that is not perpendicular to, or even substantially parallel to, to the free edges 20 of the cuffs, serving to urge the marginal portion into a bent-over configuration when the diaper is worn.

For purposes of maximizing a gasketing function pulling the cuffs and perineal barrier toward the wearer's skin, it may be desired that free distal edge 25 of transverse perineal barrier 23 is affixed to each longitudinal cuff 18 at a location within 5 mm or less, more preferably within 2 mm or less, of each free distal edge 20 of each longitudinal cuff 18. For the same purpose, and alternatively or in combination therewith, it may be desired that the perineal barrier 23 is configured such that at least one and preferably all of perineal barrier elastic members 27 are disposed with their ends or some portion proximate their ends no more than 5 mm or less, more preferably no more than 2 mm or less, of a longitudinal cuff elastic member 19. This helps create an effectively continuously elasticized, tailored gasketing structure that more closely fits the wearer's body in front and to the sides of the anus.

FIGS. 4A-4D depict transverse perineal barrier 23 extending from its attached proximal portion 24 at an angle of extension therefrom downward in the figures, i.e., toward the front portion/front waist region 12 of the diaper. In some examples such an angle may be preferred to enhance containment of urine and/or isolation of urine from stool, for example, where preservation of the integrity of a stool sample is the primary objective. In other examples, the transverse perineal barrier may be angled toward the rear of the diaper, such that it extends from its attached proximal portion toward the rear portion/rear waist region 11 of the diaper. This may enhance containment of liquid stool and/or isolation of stool from urine, for example, where preservation of the integrity of a urine sample is the primary objective.

With the diaper viewed in plan view in an extended configuration, an angle of extension of perineal barrier 23 is manifest by a longitudinal offset between the location at which the proximal portion 24 is attached to the underlying structure, and the location at which the free distal edge 25 meets the longitudinal cuffs 18. The angle of extension may be effected, as thereby suggested, by respectively attaching the proximal portion 24 of perineal barrier 23 to the underlying structure (such as the topsheet), and the distal edge 25 to the longitudinal cuffs 18, at longitudinally differing locations on the diaper.

In addition to, or in combination with, the features described above, the transverse perineal barrier 23 may generally be imparted with features, configurations and/or structures associated with cuff connectors, transverse separators and/or transverse separator sheets described in US2016/0038350; US2015/045761; US2015/045760; US2015/045759; US2015/0257946; US2015/0223996; US2015/0209195; US2014/0221955; U.S. Pat. Nos. 9,050, 219; 9,050,218; 6,786,895; 6,010,490; EP0988013A1; and EP0929277B1.

Transverse Rear Cuff

As reflected in FIGS. 1, 2A and 4, diaper 10 may include a transverse rear cuff 28c. A transverse rear cuff 28c may help the rear portion 11 of the diaper more effectively contain highly liquid stool, particularly when discharged in rapid or forceful bowel movements.

Transverse rear cuff 28c may be disposed in the rear portion 11 of the diaper. Transverse rear cuff 28c may have a proximal portion 29c and a free distal edge 30c. Free distal edge 30c of rear cuff 28c may bridge the respective free distal edges 20 of the left and right standing longitudinal cuffs 18.

Transverse rear cuff 28c may be formed of an effectively liquid impermeable material. In one example, it may be formed of a polymer film. In another example, it may be formed of an effectively liquid impermeable fibrous nonwoven web material, or a laminate of a polymer film and a fibrous nonwoven web material. In one example, rear cuff 28c may be formed of the same type material as longitudinal cuffs 18.

Transverse rear cuff 28c may be transversely affixed along the proximal portion 24 to the diaper structure by mechanical or thermal bonding, by adhesive or other means, or a combination thereof, however, use of adhesive to bond or supplementally bond proximal portion 24 to the structure may serve to provide a liquid seal at the junction between the barrier 23 and the diaper structure. In one example, proximal portion 29c of the rear cuff 28c is bonded to the rear topsheet 16r with a continuous application of adhesive therebetween, to provide a liquid seal at the junction. The adhesive may be a hot-melt type adhesive conventionally used in the manufacture of disposable diapers.

In some examples it may be desired that rear topsheet 16r and rear cuff 28c are continuously integrally joined where they meet, thereby preventing escape of liquid at the junction therebetween. In one example, an effectively liquid impervious sheet or web material (such as a polymer film) forming rear topsheet 16r in whole or in part may contiguously form a portion or layer of rear cuff 28c. It may also be desired that side edges 33c of rear cuff 28c are continuously integrally joined to the material forming longitudinal cuffs 18, thereby preventing escape of liquid at a junction therebetween.

Transverse rear cuff 28c may be manufactured to have a substantially straight free distal edge 30c and may also include one or more rear cuff elastic members 31c. In a manner similar to inclusion of longitudinal cuff elastic members 19, during manufacturing, rear cuff elastic members 31c may be incorporated and affixed into the rear cuff 28c structure in a pre-strained condition. Upon completion of manufacturing, release from the manufacturing line, and relaxation of the diaper structure, the elastic members 31c contract toward their unstrained lengths, causing the free distal edge 30c of rear cuff 28c to pull transversely against the respective free distal edges 20 of the longitudinal cuffs. When the longitudinal cuffs 18 "stand" as described above, this causes the rear cuff 28c also to "stand". This feature causes the free distal edge 30c of the rear cuff 28c to draw toward the wearer's skin above the wearer's gluteal cleft, when the diaper is worn, thereby performing a gasketing function that serves to prevent passage of liquid exudates between the cuffs 18 and out of the rear portion 11 of the diaper 10. Thus, liquid constituents of stool exudate may be prevented from escaping the diaper.

For purposes of maximizing a gasketing function pulling the distal edges 20 of longitudinal cuffs 18 and distal edge 30c of rear cuff 28c toward the wearer's skin, it may be desired that free distal edge 30c of transverse rear cuff 28c is affixed to each longitudinal cuff 18 at a location within 5 mm or less, more preferably within 2 mm or less, of each free distal edge 20 of each longitudinal cuff 18. For the same purpose, and alternatively or in combination therewith, it may be desired that the rear cuff 28c is configured such that at least one and preferably all of rear cuff elastic members 31c are disposed with their ends or some portion proximate their ends no more than 5 mm or less, more preferably no more than 2 mm or less, of a longitudinal cuff elastic member 19. This helps create an elasticized, tailored gasketing structure that more closely fits the wearer's body to the rear of the anus. In combination with the configuration of elastic members described above, a gasketing structure substantially entirely circumscribing the wearer's anus is thereby created.

Any one, combination of, or all, of the elastic members in the longitudinal cuffs, transverse perineal barrier and transverse rear cuff discussed above may be may be formed of strands (round-cross section) or strips (rectangular cross section) of elastomeric material. Suitable examples of elastomeric material include natural rubber strands as available from Easthampton Rubber Company of Stewart, Va., under the trademark L-1900 Rubber Compound; natural rubber elastic tape sold under the trademark Fulflex 9411 by Fulflex Company of Middletown, RI; polyurethane; and synthetic elastomers (e.g., LYCRA strands from Invista Corp., Wichita, KS).

Liquid Control Structure

As noted above, a liquid permeable front topsheet 16f, such as an apertured nonwoven front topsheet 16f, which may be adapted to be hydrophilic, may be preferred.

Underlying the front topsheet 16f, liquid control structure 15 is preferably configured to provide for rapid acquisition, distribution to absorbent components, and absorption of urine, quickly after a discharge. Rapid absorption of urine reduces the chance that urine may escape the front portion of the diaper to the rear portion of the diaper above the rear topsheet 16r, and contaminate stool that may be present in, or later be discharged in, the rear portion.

Accordingly, it may be desired that the liquid control structure include an acquisition layer 34 beneath the front topsheet 16f and above an absorbent layer 35. Layer 34 may have the form of, e.g., a layer, mat or other body formed of or including, e.g., comminuted cellulose fibers, or other hydrophilic natural, semi-synthetic or synthetic fibers or other material that may be used to form a mat, layer or other body. Other suitable materials for forming an acquisition layer 34 are described in, for example, U.S. Pat. App. Pub. No. 2004/0158213.

In one example, the acquisition layer 34 may include a nonwoven mat formed of fibers, which may be manufactured or adapted to be hydrophilic. In one example, acquisition layer 34 may include chemically cross-linked cellulosic fibers, which may or may not form part of a nonwoven material. In another example, acquisition layer 34 may include a nonwoven without the cross-linked cellulosic fibers. In another example, the acquisition layer may include chemically cross-linked cellulosic fibers mixed with other fibers such as natural or synthetic polymeric fibers. In some examples, such other natural or synthetic polymeric fibers may include high surface area fibers, thermoplastic binding fibers, polyethylene fibers, polypropylene fibers, PET fibers, rayon fibers, lyocell fibers, eucalyptus fibers and mixtures thereof. Suitable non-woven materials for the acquisition layer may include, but are not limited to, SMS material, including a spunbonded, a melt-blown and a further spunbonded layer. In certain examples, permanently hydrophilic nonwovens, and in particular, nonwovens with durably hydrophilic coatings are desirable. Another suitable example includes an SMMS-structure. In such examples, the nonwovens are highly porous.

The absorbent layer 35 may be formed of any absorbent material that is generally compressible, conformable, non-irritating to the wearer's skin when positioned as shown and described herein, and capable of absorbing and retaining liquids such as urine. Absorbent layer 35 may comprise a wide variety of liquid-absorbent materials commonly used in disposable diapers and other absorbent articles such as comminuted wood pulp, which is generally referred to as air felt or fluff. Examples of other suitable absorbent materials include creped cellulose wadding; melt blown polymers, including co-form; chemically stiffened, modified or cross-linked cellulosic fibers; tissue, including tissue wraps and tissue laminates, absorbent open-celled foams (such as, for example, described in U.S. Pat. Pub. No. 2015/0313770), absorbent sponges, superabsorbent polymers (such as superabsorbent fibers), absorbent gelling materials, hydrogel-forming particles, or any other known absorbent material or combination of materials. Examples of some combinations of suitable absorbent materials are cellulosic fiber fluff blended or interlaced with absorbent polymer particles, absorbent gelling materials and/or superabsorbent polymers, and absorbent gelling materials and super absorbent fibers etc. The storage layer may further comprise minor amounts (typically less than 10%) of non-liquid absorbent materials, such as adhesives, waxes, oils and the like. In some examples, the absorbent layer 35 may comprise materials and be configured as described in U.S. Patent Applications, Pub. Nos. US2014/0163511; US2014/0163503; US2014/0163501; US2014/0163500; US2012/0316526; US2012/0316528; US2014/0163501; and US2014/0371701.

The absorbent layer 35 may include absorbent polymer particles alone or in combination with other materials, such as cellulose fiber. The absorbent polymer particles may be immobilized on a substrate layer by, for example, a thermoplastic adhesive material. Absorbent polymer particles suitable for use in the absorbent layer may include any absorbent polymer particles known from superabsorbent literature, for example such as described in Modern Superabsorbent Polymer Technology, F. L. Buchholz, A. T. Graham, Wiley 1998. The absorbent polymer particles may be spherical, spherical-like, ellipsoid, or irregularly shaped, such as ovoid-shaped particles of the kind that may be obtained from inverse phase suspension polymerizations. The particles may, optionally, be agglomerated at least to some extent to form larger irregular agglomerations of particles. The absorbent polymer particles may be selected from among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in U.S. Pat. No. 5,714,156, and PCT Patent Applications Nos. WO 07/047598, WO 07/046052, WO2009/155265 and WO2009/155264. In alternative examples, the absorbent layer may be substantially cellulose-free. (Herein, "substantially cellulose free" means that the absorbent layer has less than about 10 percent by weight cellulose fiber.) Airfelt and other cellulose fiber have been used as absorbent fillers in absorbent cores of disposable diapers. Such fiber possesses absorbent properties and imparts some absorption capacity to an absorbent layer, but also may be included to provide a structural matrix to hold dispersed particles of absorbent polymer particles. While inclusion of such particles enhances absorption capacity, keeping such particles suitably dispersed may be important to prevent the particles from "gel-blocking" in use as they swell with absorbed liquid and block the passageways therebetween which allow liquid to move through deposits thereof, compromising absorption capacity. The inclusion of airfelt or other cellulose fiber as a matrix for absorbent polymer particles can serve to reduce or prevent gel-blocking. However, it also imparts bulk to an absorbent layer, even before absorption of any liquids. To reduce the overall size and/or thickness of the absorbent layer, it may be desired to construct a liquid control structure using the lowest volumes of materials possible within performance constraints. Toward this end, examples of suitable materials and constructions for a suitable absorbent structure are described in, but are not limited to, U.S. application Ser. Nos. 12/141,122; 12/141,124; 12/141,126; 12/141,128; 12/141,130; 12/141,132; 12/141,134; 12/141,141; 12/141,143; and 12/141,146; and WO2008/155699. Generally, these applications describe absorbent layer constructions that minimize or eliminate the need for and inclusion of airfelt or other forms of cellulose fiber in combination with particles of absorbent polymer particles. Suitable methods for forming deposits of absorbent polymer particles are additionally disclosed in, for example, EP1621167A2, EP1913914A2 and EP2238953A2. The absorbent polymer particles may be immobilized on the substrate layer. Immobilization may be achieved by applying a thermoplastic adhesive material, which holds and immobilizes the absorbent polymer particles, and cellulose when present, on the substrate layer. Some thermoplastic adhesive material may also penetrate into the layer of absorbent polymer particles and into the substrate layer to provide further immobilization and affixation. The thermoplastic adhesive material may not only help in immobilizing the absorbent polymer particles on the substrate layer but also may help in maintaining the integrity of any liquid channels through the structure that may be included. The thermoplastic adhesive material may help prevent migration of any substantial quantity of absorbent polymer particles into the channels. Thermoplastic adhesive materials suitable for use in the present disclosure includes hot melt adhesives including at least a thermoplastic polymer in combination with a plasticizer and other thermoplastic diluents such as tackifying resins and additives such as antioxidants. Example suitable hot melt adhesive materials are described in EP1447067A2.

Particularly in diapers for babies older than 12 months, toddlers and young children, it may be important that liquid control structure 15 have absorbent storage capacity sufficient to absorb and effectively retain a substantial quantity of urine. Accordingly, as suggested in FIG. 4A, it may be desired that absorbent layer 35 be of a size that causes it to have a substantial volume absorbent capacity. In one example, the absorbent layer 35 may extend over a majority of the plan surface area of the diaper beneath the front topsheet 16f alone, from the attached proximal portion 24 of transverse perineal barrier 23 forward. In another example, the absorbent layer 35 may extend a majority of the length of the diaper 10, and be present not only in the front portion 12 but also in the perineal portion 13 and rear portion 11, and thus be present between the backsheet and the front topsheet, and between the backsheet and the rear topsheet. For purposes of efficient, even and rapid distribution of urine across the entirety of the absorbent layer 35, it may be desired that acquisition layer 34 cover a majority of the plan surface area of the absorbent layer 35.

In some circumstances, it may be desired to use the diaper, additionally or alternatively, as a urine sample collection device. Generally in such circumstances, it may be desired that the diaper be adapted to receive and hold urine discharged by the wearer without substantially retainably absorbing the urine, and without altering the composition of the urine solution, e.g., by contaminating it with soluble materials included as or on components of the diaper in areas in which urine will be received and collected. For example, it may be desired the that the liquid control structure be adapted to provide space for urine to be received and held, but not contain substantial quantities of materials that tend to retainably absorb and/or capture urine constituents. For purposes of maintaining open space between the liquid impermeable backsheet and the wearer-facing layer to receive and hold urine, but to prevent it from flowing freely throughout the space, it may be desired that the liquid control structure include a substantially non-absorbent material, for example, a batt of material formed of an accumulation of substantially non-absorbent polymer fibers. To reduce or prevent substantial absorption and/or alteration of the composition of the urine, it may also be desired that the liquid control structure not contain a substantial quantity of water-absorbent material of any of the types typically used in disposable diapers, disposable absorbent pants and other absorbent personal hygiene products, i.e., cellulose/cellulosic fibers; absorbent sponge; absorbent foam; superabsorbent polymer; absorbent gelling material; hydrogel-forming particles; and/or absorbent polymer particles (collectively, "absorbent material"). Thus, it may be desired that at least 50 percent of the volume of the liquid control structure, as defined by its plan surface area, contain no more than 50 percent, more preferably no more than 35 percent, even more preferably no more than 20 percent, or 10 percent, or 5 percent and still more preferably no more than an insubstantial quantity or even about 0 percent, by weight absorbent material. It may be even further preferred that at least 65 percent, or 80 percent, 90 percent, 95 percent or even substantially all of the volume of the liquid control structure, as defined by its plan surface area, contain no more than 50 percent, more preferably no more than 35 percent, even more preferably no more than 20 percent, or 10 percent, or 5 percent and still more preferably no more than an insubstantial quantity or even about 0 percent, by weight absorbent material.

Non-Reliance on Adhesive-to-Skin Contact

As noted, premature and very young infants may have very sensitive and delicate skin. Adhering devices via an adhesive composition may be painfully irritating or even damaging to such an infant's skin. For this reason, it may be deemed desirable in such circumstances that the diaper 10 have no features adapted to be adhered to the wearer's skin and required for use of the diaper.

Packaging Configuration and Information

It may be desirable to provide a separate package for each individual diaper. A diaper as described herein may be deemed a product for medical use or treatment. Thus, individual packaging of each diaper may be desirable for purposes of actually or perceivably maintaining a level of sterility, cleanliness, purity and structural integrity of each individual diaper until use, in a manner similar to the manner in which, e.g., individual bandages are packaged. A supply of individually packaged diapers may be packaged as a group in a larger outer package.

In the event that a composition, for example, a water-soluble surfactant, is included in or on materials of the diaper within the space that stool will contact, it may be desirable to include information with the individual or group packaging associated with the diaper, or even on the diaper itself, effective to notify health care and/or analytical personnel of the inclusion of the composition in the diaper. Other information useful for enabling the caregiver to identify, quantify or isolate components or attributes of the stool sample recovered from the diaper may also be included with the packaging. In one additional non-limiting example, the weight of the individual diaper may be recorded on the packaging or on material(s) included with the packaging. This will enable the caregiver to calculate the quantity by weight of stool discharged by the patient, from, e.g., the weight of the diaper prior to use, and the measured weight of the diaper after its removal from the wearer following a discharge of exudate, prior to removal of the sample from the diaper. In one example, such information may be printed on the diaper itself, such as on an outward-facing surface of the backsheet or a visible layer thereof.

It may also be desirable to include information and/or indicia associated with the diaper, individual packaging (if included) or outer packaging, identifying the diaper as a special-use diaper, and distinguishing it from ordinary diapers. This will serve to notify healthcare professionals or other caregivers of the special design of the diaper, and help avoid confusion, inappropriate use of the special-use diaper for ordinary purposes, and intermixing of supplies of the special-use diapers with supplies of ordinary diapers.

Non-Invasive Method for Collecting Stool Sample from an Infant

Utilizing a suitable example of a diaper 10 as described herein, a health care professional or caregiver may obtain a stool sample from an infant by the following steps:

Applying the diaper to a patient-wearer in the same manner as a conventional disposable diaper;

Detecting a discharge of stool by the patient-wearer; this may include observing the wearer for facial, audible or body-language signals that he or she has eliminated; feeling the diaper to detect the presence of stool; or observing a change in appearance of the diaper resulting from the presence of stool;

Removing the diaper from the patient-wearer, or alternatively, removing a portion of a receptacle from the diaper;

Locating the diaper or receptacle proximate to a sample container; and

Emptying the stool from the diaper or receptacle into the sample container.

The above-described method, employing an example of a diaper as described herein, may provide improved facilitation in obtaining a stool sample from an infant, without the need for invasive devices or techniques or the application of an adhesive to the infant's skin.

Examples of Features for Urine Sample Collection

Any of the features of a diaper useful for collection of a stool sample, described above, may be included with a diaper also useful for collection of a urine sample. Features useful for collection of a urine sample are set forth in the following description.

FIGS. 9-17B depict various features that may be embodied individually or in any combination in a diaper 10. Diaper 10 may have a rear waist region 11, front waist region 12 and crotch region 13 between the front waist region and rear waist region. For reference, the lateral width of diaper 10 may be equally divided by an imaginary longitudinal axis 12-12 (FIG. 10A).

Topsheet

Diaper 10 may include a liquid control structure 15 adapted to receive and control, and in some circumstances absorb and retain liquid exudates (e.g., urine). As may be seen in FIGS. 12-14, diaper 10 may include a topsheet overlying the liquid control structure 15 such that liquid control structure 15 is disposed in the diaper between the backsheet 14 and the topsheet 16 in the front waist region 12.

Topsheet 16 may be formed of a liquid permeable material, for example, a nonwoven material such as described in U.S. Pat. No. 8,968,614. For purposes of ensuring passage of urine through the topsheet 16 to the materials of the liquid control structure 15, thereby minimizing chances of loss or contamination of a urine sample, it may be desired that the topsheet 16 be formed of an apertured nonwoven material formed of fibers. The fiber constituents may be selected or manufactured to be inherently hydrophilic, or may be treated, e.g., with an application of a suitable surfactant, to impart hydrophilic surface properties. Suitable examples of apertured topsheets are described in U.S. Pat. Nos. 7,033,340; 6,680,422; 6,498,284; 6,414,215; 5,516,572; and 5,342,338; and in pending U.S. application Ser. No. 14/270,468. In one example, synthetic polymer fiber constituents of a topsheet, such as fibers spun from polypropylene and/or polyethylene resin (ordinarily hydrophobic materials) may be treated to impart them with hydrophilic surfaces using the materials and method described in, for example, U.S. App. Pub. No. 2011/0015602. Following such treatment, the hydrophilizing materials are cross-linked and/or chemically grafted to the fiber constituents, such that they do not wash off (i.e., dissolve) in aqueous liquid (e.g., urine).

In another example, topsheet 16 may be formed of an apertured film. Use of an apertured film may be preferred, for example, in diapers for use with premature or very young and/or relatively small infants. Such diapers are typically assigned a size designation of 2 or lower, 1 or lower, or even 0 or lower. Such infants usually have relatively small bladder capacity and may discharge only small quantities of urine (e.g., less than about 50 mL) in a single discharge. The benefit of an apertured film topsheet is that it may be less likely and/or capable of retainably absorbing a substantial quantity of urine, than a topsheet formed of a fibrous nonwoven material.

In a more specific example, topsheet 16 may be formed of an apertured formed film, or in an even more specific example, a vacuum formed apertured film. Features of suitable examples of apertured films are commonly found in topsheets in currently marketed feminine hygiene pads, and are also disclosed in, for example, U.S. Pat. Nos. 8,679,391; 6,471,716; 6,989,187 and 4,629,643; and U.S. Pat. App. Pub. No. 2015/0273793.

As will be further appreciated from the description below, in some examples of the diaper herein, and in contrast to conventional disposable diapers, the patient-wearer's urine might not be absorbed in a structure beneath the topsheet to a substantial degree. Rather, following discharge, the urine may flow through the topsheet and be held substantially unabsorbed in the enveloped space between the topsheet and backsheet, until the diaper is removed from the wearer and the urine is expressed and/or poured out into a sample container. Therefore, it may be desired that the topsheet be adapted to permit the urine to move relatively freely after discharge, from the wearer-facing side of the topsheet through to the outward-facing side of the topsheet and into the envelope space, but to obstruct or inhibit urine flow back through the topsheet from the envelope space toward the wearer.

Figure 15:
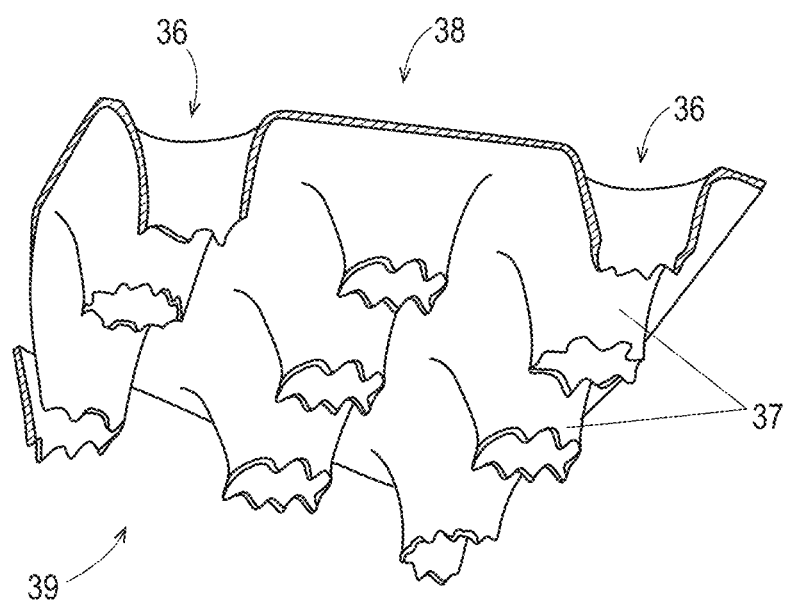
FIG. 15 is an enlarged schematic, perspective depiction of a portion of an apertured film topsheet, with apertures defined by funnel structures.
Figure 16:
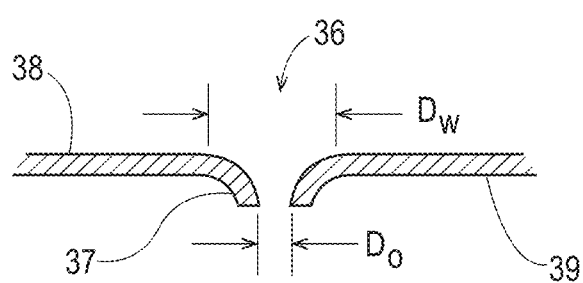
FIG. 16 is an enlarged schematic depiction of a cross section of portion of an apertured film topsheet, taken through a funnel structure.

In one example suitable for such purpose, an apertured film topsheet may be used, particularly one having a pattern of apertures 36 that are defined by funnel structures 37 as depicted in FIGS. 15 and 16. For purposes herein, a "funnel structure" is characterized as a structure defining an aperture (passageway) through the topsheet that is larger on the wearer-facing (liquid entry) side than on the outward-facing (liquid exit) side. Referring to FIG. 16, by way of non-limiting example, for apertures 36 that are circular in shape when the topsheet is viewed in plan view, the aperture/passageway on the wearer-facing side 38 of the topsheet will have diameter DW, and the aperture/passageway on the outward-facing side will have diameter DO. In the example depicted, the passageway roughly defines a cone shape. For a circular/cone-shaped funnel structure 37, DW will be greater than DO. Apertured film topsheets having such funnel structures can be manufactured by vacuum forming or otherwise as described in the above-cited references. It will be appreciated, that apertures and funnel structures need not necessarily be circular/cone-shaped; see, e.g., the various shapes for funnel structures depicted and described in U.S. Pat. No. 6,989,187. Without intending to be bound by theory, it is believed that the funnel structures, being formed of relatively thin and pliable polymeric film materials, tend to collapse toward their centers when fluid exerts pressure against the outward-facing surface 39. It is believed that this collapsing behavior causes the apertures to partially or entirely close; thus, the funnel structures function like one-way check valves that tend to permit fluid to flow through from the wearer-facing side 38 to the envelope space, and tend to obstruct or inhibit flow back through the topsheet from the envelope space, from the outward-facing side 39 and toward the wearer.

In some circumstances, it may be desired that a film topsheet not be included. Rather, a topsheet formed of nonwoven web, or even no topsheet overlying the liquid control structure, may be desirable. Particularly when use with premature infants is contemplated, a film topsheet may present a risk of sticking to the skin, which may be undesirable in some circumstances because a premature infant's skin may be very delicate.

Urine Capture Layer

As discussed above, topsheet 16, which may be adapted to allow discharged urine to freely pass therethrough, may be desired. Additionally, it may be desired that the diaper include a urine capture layer 34a beneath the topsheet 16 and above the backsheet 14.

Urine capture layer 34a may be included and may serve one or more functions: (1) to provide an open structure that occupies a volume, and thereby ensures the presence of space within the envelope structure between topsheet 16 and backsheet 14, available to receive urine while the diaper is being worn by an infant; (2) to absorb and disperse kinetic energy in a gush of urine during discharge by the wearer, thereby slowing and controlling flow thereof inside the diaper and reduce the chances of a leak; and (3) to provide a matrix structure that holds urine and restricts rapid flow back and forth within the volume occupied by the layer, reducing the chances of a leak, prior to the time the diaper is removed for urine sample retrieval.

Because a purpose of the diaper 10 as described herein may be to initially receive and collect, but then release, urine to be sampled upon removal from the patient, it may be desired that urine capture layer 34a does not have substantially absorbent properties. This may be particularly important for younger infant patients, who urinate in only relatively small volumes at a time. Accordingly, it may be desired that urine capture layer 34a be formed of or include a batt or pad of accumulated synthetic fibers spun from suitable polymeric resin(s), or a single- or multilayer section of fibrous nonwoven web material comprising fibers spun or otherwise formed of such resin(s). The resin(s) may be selected such that the fibers formed therefrom have hydrophobic surface properties, and thereby do not tend to attract or retainably hold aqueous liquid in the interstitial spaces within the fiber matrix, or otherwise, freely give up deposits of aqueous liquid upon light compression (light squeezing, rolling or wringing) of the diaper. Suitable materials and additives for forming a urine capture layer 34a are described in, for example, U.S. Pat. No. 8,598,406 and US 2004/4158213. If desired, additives and/or treatments that render the fibers hydrophilic may be omitted, to reduce the absorbency of the layer 34a. Examples of suitable synthetic, hydrophobic fibers which may be used to form all or a portion of a urine capture layer include fibers formed of one or more polyolefins (polyethylene and polypropylene). Alternatively, to promote distribution of discharged urine within the volume occupied by the liquid control structure, thereby enhancing capacity, urine capture layer 34a may be formed of or include a batt or pad (one or more layers thereof) including synthetic fibers spun or otherwise formed of materials that yield fibers that have hydrophilic surface properties. In addition to enhancing capacity, by having some attraction for aqueous liquid, hydrophilic fibers may reduce uncontrolled movement of urine back and forth within the liquid control structure. Non-limiting examples of synthetic materials that may be used to form such fibers include polyamides (e.g., nylon); polyesters (e.g., polyethylene terephthalate (PET)); polylactic acid (PLA); rayon; viscose and lyocell. In one example, urine capture layer 34a may include a blend of both hydrophilic synthetic fibers and hydrophobic fibers (such as fibers spun from polyolefins such as polypropylene and/or polyethylene). In another example, a multi-layered structure including, e.g., a layer formed predominately of synthetic hydrophobic fibers, and a layer formed predominately of hydrophobic fibers, to balance performance with respect to effective distribution of urine through the liquid control layer, and a desired level of non-absorbency and/or average Liquid Release Ratio for the diaper (described below).

Other naturally hydrophilic fiber components may be included in the urine capture layer following urination. Such components may include natural fibers, including but not limited to cellulosic fibers such as wood pulp fibers (included treated wood fibers) and cotton fibers, flax, linen and hemp fibers, and animal fibers such as wool, silk, fur and hair fibers. In another alternative, it may be desired to treat hydrophobic material(s) forming urine capture layer 34a with a surfactant composition to render their surfaces hydrophilic. In one example, synthetic polymer fiber constituents of a urine capture layer 34a, such as fibers spun from polypropylene and/or polyethylene resin (ordinarily hydrophobic materials) may be treated to impart them with hydrophilic surfaces using the materials and method described in, for example, U.S. App. Pub. No. 2011/0015602. Following such treatment, the hydrophilizing materials are cross-linked and/or chemically grafted to the fiber constituents, such that they do not wash off (i.e., dissolve) in aqueous liquid (e.g., urine).

In another example, or in combination, synthetic polymer fiber constituents of a urine capture layer 34a, such as fibers spun from polypropylene and/or polyethylene resin (ordinarily hydrophobic materials) may be treated to impart them with hydrophilic surfaces by application of one or more of the materials described in, for example, U.S. Pat. No. 8,178,748. The '748 patent identifies materials such as ARLAMOL PS15E (a PPG-15 stearyl ether formulation currently available from Croda International Plc, East Yorkshire, UK). Such a material may provide an advantage in that it imparts hydrophilicity to the surfaces of synthetic polymer fibers, while being insoluble in water and tending to remain adhered to the fiber surfaces, and thus may not dissolve or become dispersed in the desired urine sample and thereby contaminate it. Other materials that may have similar properties and advantages may include, but are not limited to, those comprising functionalities of polyethylene glycol (PEG), polypropylene glycol (PPG), and polybutylene glycol (PBG) functional groups can be used to treat a portion of the nonwoven 24 to form the hydrophilic zone 37. Nonionic surfactants having a functional group selected from the group consisting of polyethylene glycol (PEG), polypropylene glycol (PPG), polybutylene glycol (PBG), and combinations thereof can be used to treat a portion of the nonwoven 24 to form the hydrophilic zone 37. The degree of polymerization of a polyether functional group in a nonionic surfactant can be between about 2 and about 100. Because examples of such materials may be relatively stable, oily liquids that do not evaporate at room temperature within time periods in circumstances contemplated herein, it may be desired that they be applied to surfaces underlying a topsheet or other wearer-facing surface or layer, so as not to be susceptible to being rubbed off by contact with the wearer.

In conjunction with the inclusion of a soluble surfactant composition or other soluble additives, the diaper 10 can be provided with associated packaging, package insert or other media bearing information effective to notify health care and/or analytical personnel of the inclusion of the soluble surfactant composition in the diaper. Alternatively, such information may be printed on the diaper itself, in a suitably noticeable and visible location.

To reduce or prevent opportunity for substantial retaining absorption of the urine, it may be desired that the liquid control structure 15 not contain a substantial quantity of water-absorbent material of the types typically used in absorbent storage layers of disposable diapers, disposable absorbent pants and other absorbent personal hygiene products, i.e., cellulose fibers; cotton fibers, other plant fibers, absorbent sponge; absorbent foam; superabsorbent polymer; absorbent gelling material; hydrogel-forming particles; and/or absorbent polymer particles collectively herein, "absorbent material". (The term "absorbent material" as used herein is not intended to include materials not listed in the preceding sentence.) Thus, it may be desired that the volume of the liquid control structure coextensive with at least 50 percent of the plan surface area of the liquid control structure contains no more than 50 percent, more preferably no more than 35 percent, even more preferably no more than 20 percent, or 10 percent, or 5 percent and still more preferably no more than an insubstantial quantity or even about 0 percent, by weight absorbent material. It may be even further preferred that the volume of the liquid control structure coextensive with at least 65 percent, or 80 percent, 90 percent, 95 percent or even substantially all of the plan surface area of the liquid control structure contains no more than 50 percent, more preferably no more than 35 percent, even more preferably no more than 20 percent, or 10 percent, or 5 percent and still more preferably no more than an insubstantial quantity or even about 0 percent, by weight absorbent material.

It may be appreciated that the liquid control structure 15, and more particularly the urine capture layer 34*a*, may be formed of a variety of materials in a variety of sizes and/or shapes that can serve functions of a urine capture layer identified above, while avoiding stubbornly retaining absorption of urine. Accordingly, when use for obtaining a urine sample is a primary purpose of the diaper 10, it may be desired that the product have an average Liquid Release Ratio of at least 3 percent, more preferably at least 5 percent, even more preferably at least 15 percent, 25 percent, 35 percent, 45 percent, and still more preferably at least 50 percent, as measured by the Liquid Release Ratio Test Method described below. Providing a diaper product having storage space for urine provided by an envelope structure and a urine capture layer, but having limited absorption tendency, ensures that a substantial portion of urine deposited in such diaper by the wearer is recoverable by the caregiver for sampling purposes.

For purpose of obtaining a urine sample that accurately represents the urine at the time of discharge, it may be desired that the envelope space between the topsheet and backsheet contain no more than an insubstantial quantity of water-soluble materials. As a reflection of the absence of a substantial quantity of water-soluble materials, for purposes herein, purified water deposited into the diaper and then emptied out of the diaper will exhibit a conductivity no greater than 1 S/m (siemens/meter), more preferably no greater than 0.1 S/m, and even more preferably no more than 0.01 S/m, measured according to the Conductivity Test specified below. Alternatively, or in combination, the emptied water will exhibit a surface tension from 20 mN/m (milli-Newton/meter) to 72 mN/m, more preferably from 30 mN/m to 72 mN/m, even more preferably from 40 mN/m to 72 mN/m, and still more preferably from 50 mN/m to 72 mN/m, measured according to the Surface Tension Test specified below.

Waistband Member

Figure 14A:
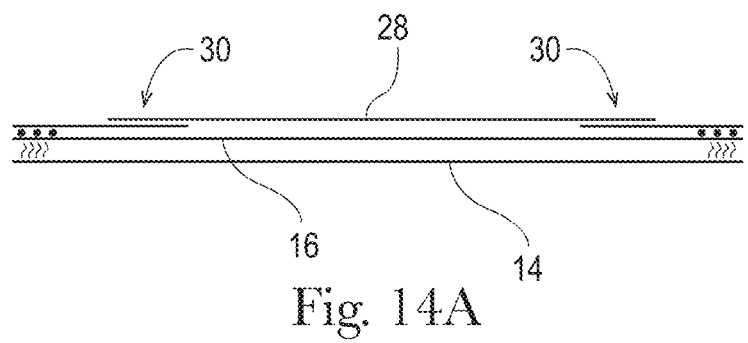
FIG. 14A is a schematic, exploded lateral cross-section of one example of the diaper shown in FIG. 10A, taken along line 14-14 shown in FIG. 10A and depicting such portion of the diaper stretched out laterally against any lateral contraction of included pre-strained elastic members.
Figure 14B:
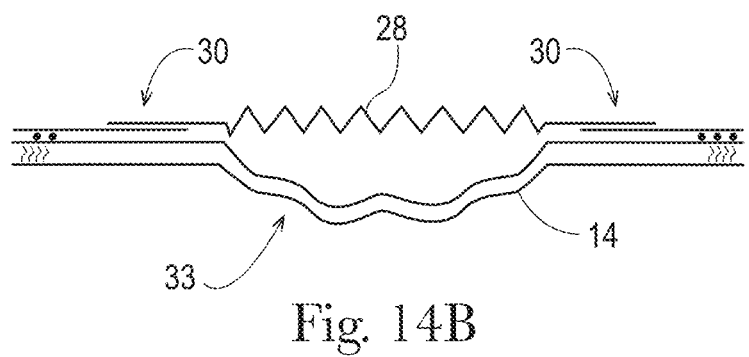
FIG. 14B is a schematic, exploded lateral cross-section of one example of diaper shown in FIG. 10A, taken along line 14-14 shown in FIG. 10A and depicting such portion of the diaper laterally contracted as might occur with the presence of included laterally pre-strained elastic members.

As reflected in FIGS. 9, 10A and 12, diaper 10 may include an elasticized waistband member 28. A waistband member 28, located as shown, may be included to serve two functions: (1) when the diaper is worn, it may provide added elastic stretch to the rear waist region 11 of the diaper, for enhancing fit and comfort; and (2) when the diaper is removed for the wearer, it may draw the rear waist region proximate the rear waist edge 29 laterally, in a manner that causes it to form a spout structure to channel urine out of the diaper at the rear. The latter effect is schematically depicted in FIGS. 14A and 14B. In FIG. 14A, the rear waist region of the diaper appears laterally extended, as it might appear while being worn. In FIG. 14B, the rear waist region of the diaper appears laterally contracted such the topsheet and backsheet form a spout structure 33. The utility of spout structure 33 will be further explained below.

Waistband member 28 may be disposed in the rear waist region 11 of the diaper, over the topsheet 16. However, it may also be disposed in the front waist region 12. It may be formed of any suitable web material. In one example, it may be formed of a nonwoven web material.

Waistband member 28 may be affixed to the diaper structure by mechanical or thermal bonding, by adhesive or other means, or a combination thereof. As may be appreciated from FIG. 14B, it may be affixed only at its laterally outboard portions 30, such that upon lateral contraction of waistband member 28, the sides of the rear waist portion of the diaper are drawn laterally inboard toward the longitudinal axis 12-12. The can cause the remaining diaper structure, such as topsheet 16 and backsheet 14, to displace to form spout structure 33.

As suggested in FIG. 10A, waistband member 28 may include one or more waistband elastic members 31. In a manner similar to inclusion of longitudinal cuff elastic members 19, during manufacturing, waistband elastic members 31 may be incorporated and affixed into the waistband member 28 structure in a pre-strained condition. Waistband member 28 may be affixed to the diaper structure by mechanical or thermal bonding, by adhesive or other means, or a combination thereof. As may be appreciated from FIG. 14B, it may be affixed only at its laterally outboard portions 30, such that upon lateral contraction of waistband member 28, the sides of the rear waist portion of the diaper are drawn laterally inboard toward the longitudinal axis 12-12. The can cause the remaining diaper structure, such as topsheet 16 and backsheet 14, to displace in a z-direction and form spout structure 33. This may be appreciated by comparison of FIGS. 14A and 14B.

When a diaper having a spout structure as described, and containing a quantity of urine following a discharge, is removed from a wearer-patient and tilted, wearer-facing surface up, toward the spout structure, the urine will tend to flow by gravity into the spout structure. This concentrates the exiting flow of the urine past the waist edge and facilitates neat pouring of the urine into a sample container.

Urine Outlet

Figure 17A:
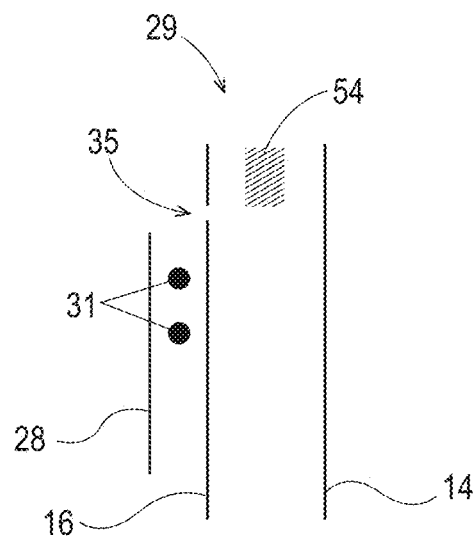
FIG. 17A is an enlarged view of a portion of the cross section indicated in circled region 17, in FIG. 12, in one example.
Figure 17B:
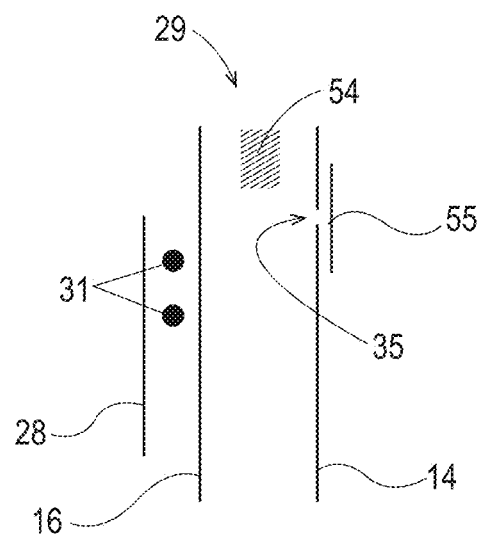
FIG. 17B is an enlarged view of a portion of the cross section indicated in circled region 17, in FIG. 12, in another example.
Figure 18:
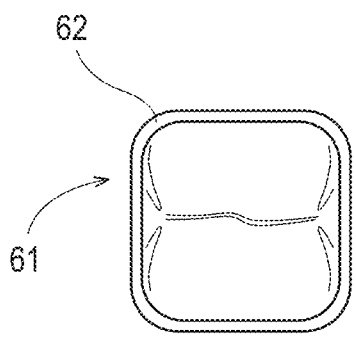
FIG. 18 is a plan view of an example of a stool sample receptacle.
Figure 19A:
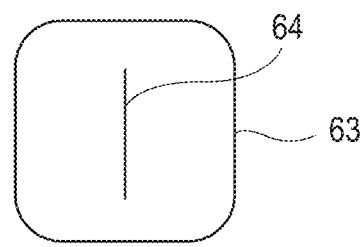
FIGS. 19A-19E are plan views of examples of stool gates.
Figure 19B:
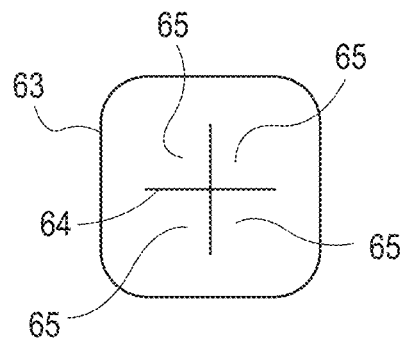
Figure 19C:
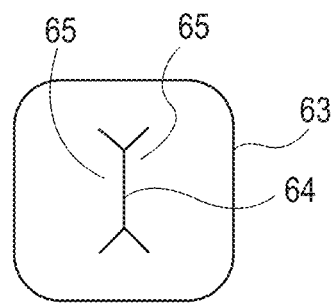
Figure 19D:
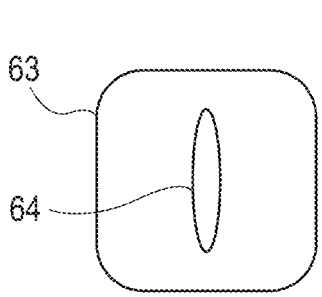
Figure 19E:
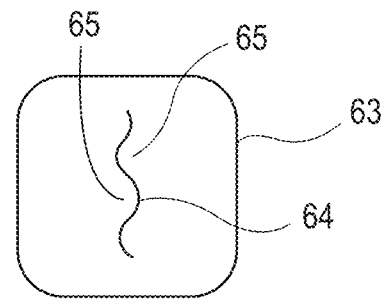

When the topsheet 16 selected for diaper 10 is highly or effectively liquid permeable for flow therethrough in both directions, it may be unnecessary to include any supplementary features to facilitate release of captured urine from the front or rear waist region of the diaper via tilting with or without compression, as described herein. However, FIGS. 17A and 17B illustrate additional features that may be included to facilitate the release of urine from the diaper, for sample collection. An outlet 35 may be cut, punched or otherwise formed in either or both of topsheet 16 and backsheet 14, in either or both of front waist region 12 and rear waist region 11, which can function to allow urine contained in the envelope space between the topsheet and backsheet to more easily and neatly be poured out of the diaper. As reflected in FIG. 17B, an outlet 35 may be accompanied by a removable or liftable outlet cover 55. Outlet cover 55 may be suitable configured to effectively prevent flow of urine out of outlet 35 until cover 55 is lifted away from the outlet 35 by the user. In one example, outlet cover 55 may be a sticker formed of liquid impermeable material, covering outlet 35 and affixed to the surrounding surfaces by adhesive. An outlet 35 may be provided in combination with the above-described spout structure 33; in one example, an outlet 35 may be located on the spout structure 33.

Packaging Configuration and Information

It may be desirable to provide a separate package for each individual diaper. A diaper as described herein may be deemed a product for medical use or treatment. Thus, individual packaging of each diaper may be desirable for purposes of actually or perceivably maintaining a level of sterility, cleanliness, purity and structural integrity of each individual diaper until use, in a manner similar to the manner in which, e.g., individual bandages are packaged. A supply of individually packaged diapers may be packaged as a group in a larger outer package.

As noted previously, in the event that a composition, for example, a water-soluble surfactant, is included in or on materials within the envelope space between the topsheet and backsheet, it may be desirable to include information with the packaging associated with the diaper, or even on the diaper itself, effective to notify health care and/or analytical personnel of the inclusion of the composition in the diaper. Other information useful for enabling health care and/or analytical personnel to identify, quantify or isolate components or attributes of the urine recovered from the diaper may also be included with the packaging. In one additional non-limiting example, the weight of the individual diaper may be recorded on the diaper, the packaging or on material(s) included/associated with the packaging. This will enable the caregiver to calculate the quantity by weight of urine discharged by the patient, from, e.g., the weight of the diaper prior to use, and the measured weight of the diaper after its removal from the wearer following a discharge of urine, prior to taking of a urine sample from the diaper. In one example, such information may be printed on the diaper itself, such as on an outward-facing surface of the backsheet or a visible layer thereof.

It may also be desirable to include information and/or indicia associated with the diaper, individual packaging (if included) or outer packaging, identifying the diaper as a special-use diaper, and distinguishing it from ordinary diapers. This will serve to notify healthcare professionals or other caregivers of the special design of the diaper, and help avoid confusion, inappropriate use of the special-use diaper for ordinary purposes, and intermixing of supplies of the special-use diapers with supplies of ordinary diapers.

Non-Invasive Method for Obtaining a Urine Sample from an Infant

Utilizing a suitable example of a diaper 10 as described herein, a caregiver may obtain a sample of urine from an infant patient by the following steps:

Applying a diaper to a patient-wearer in substantially the same manner as one would apply an ordinary disposable diaper;

Detecting a discharge of urine by the patient-wearer; this may include observing the patient-wearer for facial, audible or body-language signals that he or she has urinated; feeling the diaper to detect the presence of urine; or observing a change in appearance of the diaper resulting from the visible presence or urine or activation of a wetness indicator included with the diaper;

Removing the diaper from the patient-wearer;

Locating the diaper over or proximate to a sample container;

Tilting the diaper such that one of the front waist region and the rear waist region is lower than the other, which orientation may be selected according to, for example, the location of an outlet and/or a spout structure in the front waist region or the rear waist region; and Pouring urine contained in the diaper from the lower of the front waist region and the rear waist region, into the sample container.

In some examples, the caregiver may incorporate the step of compressing the diaper, by wringing the diaper, rolling the diaper or otherwise, before, during or after the tilting step, to facilitate expulsion of urine from the envelope space in the diaper and thereby urge it out of the diaper.

Optionally, a step of creating a urine outlet opening in the envelope structure of the diaper to facilitate release of urine, following the removing step, may be included.

The step may involve cutting such an opening in the structure using a cutting instrument, or alternatively, lifting a cover 55 from a urine outlet 35 already included on the diaper, as described above.

The above-described method, employing any example of a diaper described herein, may provide improved facilitation in obtaining a urine sample from an infant, without the need for invasive devices or techniques, or the application of an adhesive to the infant's skin.

The diapers contemplated herein may find utility, in some examples, in circumstances involving medical diagnosis, medical treatment and/or medical research involving very young, small and/or prematurely-born infants. As such, it may be desired to combine any of the features described herein with features described in U.S. application Ser. No. 15/234,540, or in the application filed on the same day as the filing hereof, entitled CONFIGURABLE ABSORBENT ARTICLES HAVING IMPROVED BODILY EXUDATE SEPARATION AND SAMPLING.

Liquid Release Ratio Test Method

The Liquid Release Ratio Test Method measures the volume of saline solution that can be drained from a diaper after loading it with a known volume of saline solution.

Begin by removing the individual diaper samples from any packaging, and allow them to precondition at 25° C.±2 C.° and 50%±2% relative humidity for 2 hours prior to testing. Testing is performed under these same conditions. Following preconditioning, each diaper is tested as follows. Saline solution or water used for testing also should be at a temperature of 25° C.±2 C°.

1. Provide a calibrated graduated cylinder capable of measuring liquid volume contained therein to the nearest 1.0 mL.
2. Provide a rectangular sheet of rigid, nonabsorbent material having a flat surface (for example, a 5 mm thick LEXAN or PLEXIGLAS sheet), of a size at least as large in both dimensions in the x-y plane, as the diaper samples to be tested, in fully extended configuration.
3. Extend the diaper sample to its full dimensions along both directions in the x-y plane and affix it to the sheet, with the rear waist edge of the diaper aligned with an edge of the sheet. The diaper can be affixed to the sheet using Velcro hook-and-loop material, tape, clamps or any other device effective to grip or attach to the diaper along its edges, and fix the diaper in place on the sheet in its extended configuration. Do not apply any affixing devices directly over or under the liquid control structure.
4. If the diaper has a topsheet overlying the liquid control structure, cut a neat 1-cm square hole in the topsheet, at the rearwardmost extent of the envelope space containing the liquid control structure, with opposing corners aligned with and sides oriented diagonally to (at 45-degree angles with) the longitudinal axis of the diaper. This is to provide an outlet for draining liquid, in the draining step below.
5. Lay the sheet with the affixed diaper, wearing-facing surface up, on a horizontal work table. Locate a receiving point on the topsheet, along the longitudinal axis of the diaper, and 100 mm from the front waist edge.
6. Pour 30 mL of 0.9% saline solution (NaCl+deionized water) in a single focused stream from an approximate height of 1 inch above the topsheet, onto the receiving point, at a rate no greater than 10 mL/sec and no less than 20 mL/sec.

7. Let the diaper rest for 60 seconds following delivery of all 30 mL of the saline solution to the diaper.
8. Immediately after the resting period, move the edge of the sheet adjacent the diaper rear waist edge, to the edge of the table. Locate the graduated cylinder below the edge of the table in a position suitable to receive liquid drained from the diaper, and lift the edge of the sheet adjacent the front waist edge of the diaper (which is still affixed to the sheet) so that the sheet and the diaper are tilted, front waist edge up, at an angle 45 degrees from horizontal. Allow liquid to drain from the diaper into the cylinder, for 60 seconds after tilting. (If necessary, a plastic funnel may be used to direct the liquid into the cylinder and ensure that none is spilled.)
9. Record the volume of liquid collected in the cylinder, to the nearest mL. Calculate the liquid release ratio for the sample as the volume of saline solution drained from the diaper, divided by 30 mL, and multiplying by 100%.

Repeat this procedure for 10 diaper samples. Calculate the average Liquid Release Ratio exhibited by the 10 samples and report the value to the nearest 0.1%.

Conductivity Test Method

To obtain the test samples, follow all steps of the Liquid Release Ratio Test Method, above, except substitute Type 1 reagent grade water for saline solution, in Step 6. Step 9 (volume measurement), and the liquid release ratio calculation, are not required.

Ensure that the liquid sample drained from the diaper is at a temperature of 25° C. Measure the conductivity of a sample obtained from each of 10 diaper samples, and record and calculate the average of the results. Conductivity may be measured using any suitable device adapted for this purpose, and adapted for testing for values within the ranges set forth in the specification above, for example, a conductivity meter available from Myron L Company, Carlsbad, California Surface Tension Test Method To obtain the test samples, follow all steps of the Liquid Release Ratio Test Method, above, except substitute Type 1 reagent grade water for saline solution, in Step 6. Step 9 (volume measurement), and the liquid release ratio calculation, are not required.

Ensure that the liquid sample drained from the diaper is at a temperature of 25° C. Measure the surface tension of a sample obtained from each of 10 diaper samples, and record and calculate the average of the results. Surface tension may be measured using any suitable device adapted for this purpose, and adapted for testing for values within the ranges set forth in the specification above, for example, a surface tensiometer available from Kibron Inc., Helsinki, Finland.

Opacity Test Method

The opacity of a backsheet material or receptacle material is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab LabScan XE running Universal Software (available from Hunter Associates Laboratory Inc., Reston, VA). Instrument calibration and measurements are made using the standard white and black calibration plates provided by the vendor. All testing is performed in a room maintained at about 23±2° C. and about 50±2% relative humidity.

Configure the spectrophotometer for the XYZ color scale, D65 illuminant, 10° standard observer, with UV filter set to nominal. Standardize the instrument according to the manufacturer's procedures using the 1.20 inch port size and 1.00 inch area view. After calibration, set the software to the Y opacity procedure.

To obtain the specimen of a backsheet material, lay the diaper sample flat on a bench, body facing surface downward, and measure the total longitudinal length of the diaper. Note a site 33% of the total length from the rear waist edge of the diaper along the longitudinal axis. Carefully remove the backsheet including any and all laminate components thereof, from the outward-facing side of the diaper. A cryogenic spray, such as Cyto-Freeze (obtained from Control Company, Houston, TX), may be used to separate the backsheet laminate from the other components of the diaper. Cut a piece 50.8 mm by 50.8 mm centered at the site identified above. A 50.8 mm by 50.8 mm specimen of a receptacle bag material may be obtained by cutting the specimen away from the bag structure. Precondition specimens at about 23° C.±2 C.° and about 50%±2% relative humidity for 2 hours prior to testing.

Place the specimen over the measurement port. The specimen should completely cover the port with the surface corresponding to the garment-facing surface of the diaper directed toward the port. Cover the specimen with the white standard plate. Take a reading, then remove the white tile and replace it with black standard tile without moving the specimen. Obtain a second reading, and calculate the opacity as follows:

$$\text{Opacity} = Y \text{ value(black backing)} / Y \text{ value(white backing)} \times 100$$

A total of 10 identical diapers are analyzed and their opacity results recorded. Calculate and report the average opacity and standard deviation for the 10 backsheet laminate measurements to the nearest 0.01%.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of the present disclosure.

What is claimed is:

1. A disposable diaper having a length, a front portion, a rear portion, and a perineal portion between the front and rear portions, the diaper comprising:
   a backsheet comprising an effectively liquid impermeable material;

a liquid control structure disposed over at least a portion the backsheet;

a topsheet disposed over the liquid control structure;

a pass-through port disposed at least partially in the rear portion of the diaper; and a sample collection receptacle, wherein the sample collection receptacle is a bag structure comprising an open end and a closed end, and wherein the sample collection receptacle is formed of a liquid impermeable polymeric film.

2. The diaper of claim 1, wherein the liquid control structure is disposed only in the front portion of the diaper.

3. The diaper of claim 1, comprising left and right standing longitudinal cuffs each extending from the front portion to the rear portion and having a proximal cuff portion, and a free longitudinal cuff distal edge, each longitudinal cuff comprising a longitudinal cuff elastic member proximate the free longitudinal cuff distal edge, the longitudinal cuff elastic member being incorporated into the longitudinal cuff in a pre-strained condition so as to cause material forming the free longitudinal cuff distal edge to gather and extend toward a wearer's skin when the diaper is worn.

4. The diaper of claim 3, wherein the longitudinal cuffs comprise effectively liquid impermeable material.

5. The diaper of claim 3, wherein the longitudinal cuffs comprise polymeric film.

6. The diaper of claim 1, wherein the sample collection receptacle is sealingly affixed to an outer perimeter of the pass-through port.

7. The diaper of claim 6, wherein the sample collection receptacle is sealingly affixed to a portion of the backsheet.

8. A disposable diaper having a length, a front portion, a rear portion, and a perineal portion between the front and rear portions, the disposable diaper comprising:

a backsheet comprising an effectively liquid impermeable material;

a liquid control structure disposed over the backsheet;

a rear upper layer comprising an effectively liquid impermeable material disposed at least partially in the rear portion of the diaper;

a pass-through port disposed at least partially in the rear portion of the diaper; and a sample collection receptacle, wherein the sample collection receptacle is a bag structure comprising an open end and a closed end, and wherein the sample collection receptacle is formed of a liquid impermeable polymeric film.

9. The diaper of claim 8, wherein the rear upper layer comprises polymeric film.

10. The diaper of claim 8, wherein the liquid control structure is disposed only in the front portion and the perineal portion of the diaper.

11. The diaper of claim 10, comprising a front upper layer comprising an effectively liquid permeable material, overlying the liquid control structure in the front portion and the perineal portion of the diaper.

12. The diaper of claim 8, wherein the liquid control structure is disposed only in the front portion of the diaper.

13. The diaper of claim 12, comprising a front upper layer comprising an effectively liquid permeable material, overlying the liquid control structure in the front portion.

14. The diaper of claim 8, comprising left and right standing longitudinal cuffs each extending from the front portion to the rear portion and having a proximal cuff portion, and a free longitudinal cuff distal edge, each longitudinal cuff comprising a longitudinal cuff elastic member proximate the free longitudinal cuff distal edge, the longitudinal cuff elastic member being incorporated into the longitudinal cuff in a pre-strained condition so as to cause material forming the free longitudinal cuff distal edge to gather and extend toward a wearer's skin when the diaper is worn.

15. The diaper of claim 14, wherein the longitudinal cuffs comprise effectively liquid impermeable material.

16. The diaper of claim 15, wherein the longitudinal cuffs comprise polymeric film.

17. The diaper of claim 8, wherein the sample collection receptacle is sealingly affixed to an outer perimeter of the pass-through port.

18. The diaper of claim 17, wherein the sample collection receptacle is sealingly affixed to a portion of the backsheet.

* * * * *